(12) United States Patent
McClain et al.

(10) Patent No.: US 9,539,593 B2
(45) Date of Patent: Jan. 10, 2017

(54) HOLDER FOR ELECTRICALLY CHARGING A SUBSTRATE DURING COATING

(75) Inventors: James B. McClain, Raleigh, NC (US); Doug Taylor, Franklinton, NC (US); Ed Dickinson, Waltham, MA (US); Steve Worm, Raleigh, NC (US)

(73) Assignee: Micell Technologies, Inc., Durham, NC (US)

(*) Notice: Subject to any disclaimer, the term of this patent is extended or adjusted under 35 U.S.C. 154(b) by 1333 days.

(21) Appl. No.: 11/877,591

(22) Filed: Oct. 23, 2007

(65) Prior Publication Data

US 2008/0095919 A1    Apr. 24, 2008

Related U.S. Application Data

(60) Provisional application No. 60/862,592, filed on Oct. 23, 2006.

(51) Int. Cl.
| | | |
|---|---|---|
| B05C 13/02 | (2006.01) | |
| B05B 5/053 | (2006.01) | |
| A61L 31/10 | (2006.01) | |
| B05B 5/08 | (2006.01) | |

(52) U.S. Cl.
CPC ............. B05B 5/0533 (2013.01); A61L 31/10 (2013.01); B05B 5/082 (2013.01); B05C 13/025 (2013.01)

(58) Field of Classification Search
CPC .................................................. B05C 13/025
USPC ................................................. 118/300, 500
See application file for complete search history.

(56) References Cited

U.S. PATENT DOCUMENTS

| | | |
|---|---|---|
| 3,087,660 A | 4/1963 | Endicott |
| 3,087,860 A | 4/1963 | Endicott |
| 3,123,077 A | 3/1964 | Alcamo |
| 3,457,280 A | 7/1969 | Schmitt et al. |
| 3,597,449 A | 8/1971 | Deprospero et al. |

(Continued)

FOREIGN PATENT DOCUMENTS

| | | |
|---|---|---|
| CA | 2589761 | 12/2004 |
| CA | 2615452 A1 | 1/2007 |

(Continued)

OTHER PUBLICATIONS

PCT/US07/10227 Search Report mailed Aug. 8, 2008.

(Continued)

*Primary Examiner* — Dah-Wei D Yuan
*Assistant Examiner* — Stephen Kitt
(74) *Attorney, Agent, or Firm* — Lerner, David, Littenberg, Krumholz & Mentlik, LLP

(57) ABSTRACT

A stent holder for mounting and electrically charging a stent during coating of the stent using dry particles, the particles comprising inert polymers, pharmaceutical or biological agents, is provided. An assembly for supporting and electrically charging a stent during the coating of the stent using dry particles, the particles comprising inert polymers, pharmaceutical or biological agents, is provided. A chamber for creating an electrical field around a stent and for supporting, electrically charging, and exposing the stent to dry particles, the particles comprising inert polymers, pharmaceutical or biological agents, is provided. A method for creating an electrical field around a stent and for supporting, electrically charging, and exposing the stent to dry particles comprising inert polymers, pharmaceutical or biological agents is provided.

13 Claims, 19 Drawing Sheets

(56) References Cited

U.S. PATENT DOCUMENTS

| | | | |
|---|---|---|---|
| 3,929,992 A | 12/1975 | Sehgal et al. |
| 4,000,137 A | 12/1976 | Dvonch et al. |
| 4,285,987 A | 8/1981 | Ayer et al. |
| 4,326,532 A | 4/1982 | Hammar |
| 4,336,381 A | 6/1982 | Nagata et al. |
| 4,582,731 A | 4/1986 | Smith |
| 4,655,771 A | 4/1987 | Wallsten |
| 4,733,665 A | 3/1988 | Palmaz |
| 4,734,227 A | 3/1988 | Smith |
| 4,734,451 A | 3/1988 | Smith |
| 4,931,037 A | 6/1990 | Wetterman |
| 4,950,239 A | 8/1990 | Gahara |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,106,650 A | 4/1992 | Hoy et al. |
| 5,158,986 A | 10/1992 | Cha et al. |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,324,049 A * | 6/1994 | Mistrater et al. ............ 279/2.17 |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,556,383 A | 9/1996 | Wang et al. |
| 5,562,922 A | 10/1996 | Lambert |
| 5,569,463 A | 10/1996 | Helmus et al. |
| 5,609,629 A | 3/1997 | Fearnot et al. |
| 5,626,611 A | 5/1997 | Liu et al. |
| 5,626,862 A | 5/1997 | Brem et al. |
| 5,674,242 A | 10/1997 | Phan et al. |
| 5,725,570 A | 3/1998 | Heath |
| 5,800,511 A | 9/1998 | Mayer |
| 5,811,032 A | 9/1998 | Kawai et al. |
| 5,824,049 A | 10/1998 | Ragheb et al. |
| 5,837,313 A | 11/1998 | Ding et al. |
| 5,873,904 A | 2/1999 | Ragheb et al. |
| 5,876,426 A | 3/1999 | Kume et al. |
| 5,924,631 A | 7/1999 | Rodrigues et al. |
| 5,948,020 A | 9/1999 | Yoon et al. |
| 5,957,975 A | 9/1999 | Lafont et al. |
| 6,013,855 A | 1/2000 | McPherson et al. |
| 6,077,880 A | 6/2000 | Castillo et al. |
| 6,129,755 A | 10/2000 | Mathis et al. |
| 6,143,037 A | 11/2000 | Goldsten et al. |
| 6,143,314 A | 11/2000 | Chandrashekar et al. |
| 6,146,356 A | 11/2000 | Wang et al. |
| 6,146,404 A | 11/2000 | Kim et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,206,914 B1 | 3/2001 | Soykan et al. |
| 6,231,600 B1 | 5/2001 | Zhong et al. |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,273,913 B1 | 8/2001 | Wright et al. |
| 6,284,758 B1 | 9/2001 | Egi et al. |
| 6,309,669 B1 | 10/2001 | Setterstrom et al. |
| 6,319,541 B1 | 11/2001 | Pletcher et al. |
| 6,336,934 B1 * | 1/2002 | Gilson et al. ................ 606/200 |
| 6,342,062 B1 | 1/2002 | Suon et al. |
| 6,355,691 B1 | 3/2002 | Goodman |
| 6,358,556 B1 | 3/2002 | Ding et al. |
| 6,361,819 B1 | 3/2002 | Tedeschi et al. |
| 6,364,903 B2 | 4/2002 | Tseng et al. |
| 6,368,658 B1 | 4/2002 | Schwarz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D-Augustine et al. |
| 6,448,315 B1 | 9/2002 | Lidgren et al. |
| 6,461,644 B1 | 10/2002 | Jackson et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,517,860 B1 | 2/2003 | Rosser et al. |
| 6,521,258 B1 | 2/2003 | Mandel et al. |
| 6,524,698 B1 | 2/2003 | Schmoock |
| 6,537,310 B1 | 3/2003 | Palmaz et al. |
| 6,541,033 B1 | 4/2003 | Shah |
| 6,572,813 B1 | 6/2003 | Zhang et al. |
| 6,575,933 B1 * | 6/2003 | Wittenberger et al. .. 604/101.02 |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hanson et al. |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Chen et al. |
| 6,726,712 B1 | 4/2004 | Raeder-Devens et al. |
| 6,736,996 B1 | 5/2004 | Carbonell et al. |
| 6,743,505 B2 | 6/2004 | Antall et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang et al. |
| 6,780,475 B2 | 8/2004 | Fulton et al. |
| 6,800,663 B2 | 10/2004 | Asgarzadeh et al. |
| 6,815,218 B1 | 11/2004 | Jacobsen et al. |
| 6,821,549 B2 | 11/2004 | Jayaraman |
| 6,837,611 B2 | 1/2005 | Kuo et al. |
| 6,838,089 B1 | 1/2005 | Carlsson et al. |
| 6,838,528 B2 | 1/2005 | Zhou et al. |
| 6,858,598 B1 | 2/2005 | McKearn et al. |
| 6,860,123 B1 | 3/2005 | Uhlin et al. |
| 6,868,123 B2 | 3/2005 | Bellas et al. |
| 6,884,377 B1 | 4/2005 | Burnham et al. |
| 6,884,823 B1 | 4/2005 | Plerick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,939,569 B1 | 9/2005 | Green et al. |
| 6,973,718 B2 | 12/2005 | Sheppard et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,308,748 B2 | 12/2007 | Kokish |
| 7,326,734 B2 | 2/2008 | Zi et al. |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |

(56) References Cited

U.S. PATENT DOCUMENTS

| | | |
|---|---|---|
| 7,462,593 B2 | 12/2008 | Cuttitta et al. |
| 7,485,113 B2 | 2/2009 | Varner et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,763,277 B1 | 7/2010 | Canham et al. |
| 7,837,726 B2 | 11/2010 | Von Oepen et al. |
| 7,919,108 B2 | 4/2011 | Rees et al. |
| 7,955,383 B2 | 6/2011 | Krivoruchko et al. |
| 7,972,661 B2 | 7/2011 | Pui et al. |
| 2001/0026804 A1 | 10/2001 | Boutignon |
| 2001/0034336 A1 | 10/2001 | Shah et al. |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworn et al. |
| 2002/0133072 A1 | 9/2002 | Wang et al. |
| 2002/0144757 A1 | 10/2002 | Craig et al. |
| 2003/0001830 A1 | 1/2003 | Wampler et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1* | 1/2004 | Epstein et al. ............... 427/2.24 |
| 2004/0018228 A1 | 1/2004 | Fischell et al. |
| 2004/0022853 A1 | 2/2004 | Ashton et al. |
| 2004/0044397 A1 | 3/2004 | Stinson |
| 2004/0059290 A1 | 3/2004 | Palasis et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0144317 A1 | 7/2004 | Chuman et al. |
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0069630 A1* | 3/2005 | Fox et al. ................ 118/500 |
| 2005/0070990 A1 | 3/2005 | Stinson |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131513 A1 | 6/2005 | Myers |
| 2005/0147334 A1 | 7/2005 | Kanazawa et al. |
| 2005/0147734 A1 | 7/2005 | Seppala et al. |
| 2005/0166841 A1* | 8/2005 | Robida ................ 118/500 |
| 2005/0175772 A1* | 8/2005 | Worsham et al. .......... 118/300 |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0216075 A1 | 9/2005 | Wang et al. |
| 2005/0238829 A1 | 10/2005 | Motherwell et al. |
| 2005/0238839 A1 | 10/2005 | Takagi et al. |
| 2005/0255327 A1 | 11/2005 | Chaney |
| 2005/0260186 A1 | 11/2005 | Bookbinder et al. |
| 2005/0268573 A1 | 12/2005 | Yan |
| 2005/0288481 A1 | 12/2005 | Desnoyer et al. |
| 2006/0001011 A1 | 1/2006 | Wilson et al. |
| 2006/0020325 A1 | 1/2006 | Burgermeister et al. |
| 2006/0030652 A1 | 2/2006 | Adams et al. |
| 2006/0045901 A1 | 3/2006 | Weber et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0116755 A1 | 6/2006 | Stinson |
| 2006/0121089 A1 | 6/2006 | Michal et al. |
| 2006/0134211 A1 | 6/2006 | Lien et al. |
| 2006/0136041 A1 | 6/2006 | Schmid et al. |
| 2006/0147611 A1* | 7/2006 | Coye et al. .................... 427/2.1 |
| 2006/0147698 A1 | 7/2006 | Carroll et al. |
| 2006/0153729 A1 | 7/2006 | Stinson |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0276877 A1 | 12/2006 | Owens et al. |
| 2007/0009564 A1 | 1/2007 | McClain et al. |
| 2007/0032864 A1 | 2/2007 | Furst et al. |
| 2007/0038227 A1 | 2/2007 | Massicotte et al. |
| 2007/0059350 A1 | 3/2007 | Kennedy et al. |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154554 A1 | 7/2007 | Burgermeister et al. |
| 2007/0196423 A1 | 8/2007 | Ruane et al. |
| 2007/0198081 A1 | 8/2007 | Castro et al. |
| 2007/0203569 A1 | 8/2007 | Burgermeister et al. |
| 2007/0259017 A1 | 11/2007 | Francis |
| 2007/0280992 A1 | 12/2007 | Margaron et al. |
| 2008/0051866 A1 | 2/2008 | Chen et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0255510 A1 | 10/2008 | Wang |
| 2008/0269449 A1 | 10/2008 | Chattopadhyay et al. |
| 2008/0292776 A1 | 11/2008 | Dias et al. |
| 2008/0300669 A1 | 12/2008 | Hossainy |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet et al. |
| 2009/0082855 A1 | 3/2009 | Borges et al. |
| 2009/0098178 A1 | 4/2009 | Hofmann et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |

(56) References Cited

U.S. PATENT DOCUMENTS

| | | |
|---|---|---|
| 2009/0227949 A1 | 9/2009 | Freyman et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0297578 A1 | 12/2009 | Trollsas et al. |
| 2010/0015200 A1 | 1/2010 | McClain et al. |
| 2010/0030261 A1 | 2/2010 | McClain et al. |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0272778 A1 | 10/2010 | McClain et al. |
| 2010/0298928 A1 | 11/2010 | McClain et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja |
| 2011/0190864 A1 | 8/2011 | McClain et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0172787 A1 | 7/2012 | McClain et al. |
| 2012/0177742 A1 | 7/2012 | McClain et al. |
| 2012/0271396 A1 | 10/2012 | Zheng et al. |
| 2012/0280432 A1 | 11/2012 | Chen et al. |
| 2012/0323311 A1 | 12/2012 | McClain et al. |
| 2013/0085515 A1 | 4/2013 | To et al. |

FOREIGN PATENT DOCUMENTS

| | | |
|---|---|---|
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 1465410 | 1/2004 |
| CN | 1575860 A | 2/2005 |
| CN | 1649551 | 8/2005 |
| CN | 1684641 A | 10/2005 |
| CN | 1756575 A | 4/2006 |
| CN | 1946452 A | 4/2007 |
| EP | 0604022 | 6/1994 |
| EP | 0982041 | 3/2000 |
| EP | 1195822 A2 | 4/2002 |
| EP | 1325758 A2 | 7/2003 |
| EP | 1454677 | 9/2004 |
| EP | 2197070 A1 | 6/2010 |
| EP | 2293357 A1 | 3/2011 |
| EP | 2293366 A1 | 3/2011 |
| JP | 1994-098902 | 4/1994 |
| JP | 06218063 | 8/1994 |
| JP | H09-056807 | 3/1997 |
| JP | 10005345 | 1/1998 |
| JP | 2003533492 | 11/2001 |
| JP | 2003-205037 | 7/2003 |
| JP | 2003-533286 | 11/2003 |
| JP | 2003533492 | 11/2003 |
| JP | 2003533493 A | 11/2003 |
| JP | 2004512059 A | 4/2004 |
| JP | 2004/173770 | 6/2004 |
| JP | 2004-518458 | 6/2004 |
| JP | 2004-529674 | 9/2004 |
| JP | 2005-505318 | 2/2005 |
| JP | 2005-523119 | 8/2005 |
| JP | 2005-5233332 | 8/2005 |
| JP | 2005-296690 | 10/2005 |
| JP | 2006506191 A | 2/2006 |
| JP | 2007502281 A | 2/2007 |
| JP | 2009-501566 | 1/2009 |
| JP | 2009525768 A | 7/2009 |
| WO | WO-2011-009096 A1 | 1/1920 |
| WO | WO-95/06487 | 3/1995 |
| WO | WO 96/20698 | 7/1996 |
| WO | WO 97/45502 | 12/1997 |
| WO | WO-01/54662 | 8/2001 |
| WO | WO-01/87371 | 11/2001 |
| WO | WO-01/87372 | 11/2001 |
| WO | WO-02/40702 | 5/2002 |
| WO | WO-02/43799 | 6/2002 |
| WO | 02074194 A2 | 9/2002 |
| WO | WO-02/090085 | 11/2002 |
| WO | WO-03/039553 | 5/2003 |
| WO | 03082368 A1 | 10/2003 |
| WO | WO-03/101624 A1 | 12/2003 |
| WO | 2004009145 A1 | 1/2004 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | WO-2005-042623 A1 | 5/2005 |
| WO | WO-2005/063319 | 7/2005 |
| WO | WO-2005/069889 | 8/2005 |
| WO | WO-2005-117942 A2 | 12/2005 |
| WO | WO-2006/014534 | 2/2006 |
| WO | WO-2006/052575 | 5/2006 |
| WO | WO-2006/065685 | 6/2006 |
| WO | WO-2006-083796 A2 | 8/2006 |
| WO | WO-2006-099276 A2 | 9/2006 |
| WO | WO-2007-002238 | 1/2007 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO-2007/092179 | 8/2007 |
| WO | WO 2007/143609 | 12/2007 |
| WO | WO-2008/042909 | 4/2008 |
| WO | WO-2008-046641 | 4/2008 |
| WO | WO-2008-046642 | 4/2008 |
| WO | WO-2008/052000 | 5/2008 |
| WO | WO-2008/070996 | 6/2008 |
| WO | WO 2008/086369 | 7/2008 |
| WO | WO-2008-131131 A1 | 10/2008 |
| WO | WO-2008/148013 | 12/2008 |
| WO | 2009051614 A1 | 4/2009 |
| WO | WO-2009/051780 | 4/2009 |
| WO | WO-2009/146209 | 12/2009 |
| WO | WO 2010/009335 | 1/2010 |
| WO | WO-2010/075590 | 7/2010 |
| WO | WO-2010-111196 A2 | 9/2010 |
| WO | WO-2010-111196 A3 | 9/2010 |
| WO | WO-2010-111232 A2 | 9/2010 |
| WO | WO-2010-111232 A9 | 9/2010 |
| WO | WO-2010-111238 A2 | 9/2010 |
| WO | WO-2010-111238 A3 | 9/2010 |
| WO | WO-2010-120552 A2 | 10/2010 |
| WO | WO-2010-120552 A3 | 10/2010 |
| WO | WO-2010-121187 A2 | 10/2010 |
| WO | WO-2010-121187 A3 | 10/2010 |
| WO | 2010136604 A1 | 12/2010 |
| WO | WO-2011/097103 | 8/2011 |
| WO | WO-2011/119762 | 9/2011 |
| WO | WO-2011/130448 | 10/2011 |
| WO | WO-2011/133655 | 10/2011 |

(56) References Cited

FOREIGN PATENT DOCUMENTS

| WO | WO-2012/009684 | 1/2012 |
|---|---|---|
| WO | WO-2012/034079 | 3/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |

OTHER PUBLICATIONS

PCT/US2011/032371, International Search Report dated Jul. 7, 2011.
PCT/US09/41045 Search Report dated Aug. 11, 2009.
PCT/US08/11852 Search Report dated Dec. 19, 2008.
PCT/US08/64732 Search Report dated Sep. 4, 2008.
PCT/US08/60671 Search Report dated Sep. 5, 2008.
PCT/US08/50536 Search Report dated Jun. 2, 2008.
PCT/US07/80213 Search Report dated Apr. 16, 2008.
PCT/US09/50883 Search Report dated Nov. 17, 2009.
PCT/US07/82275 Search Report mailed Apr. 18, 2008.
PCT/US06/27322 Search Report mailed Apr. 25, 2007.
PCT/US06/27321 Search Report mailed Oct. 16, 2007.
PCT/US06/24221 Search Report mailed Jan. 29, 2007.
McAlpine, J.B. et al., "Revised NMR Assignments for Rapamycin," J. Antibiotics 44:688-690 (1991).
Ong and Serruys, "Technology Insight: an overview of research in drug-eluting stents," Nat. Clin. Parct. Cardiovas. Med. 2(12):647 (2005).
Latella et al., "Nanoindentation hardness. Young's modulus, and creep behavior of organic-inorganic silica-based sol-gel thin films on copper," J Mater Res 23(9): 2357-2365 (2008).
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 3, 2001] http://www.lib0ev.de/p1/pdf/EN14299.pdf (2009).
Szabadits et al., "Flexibility and trackability of laser cut coronary stent systems," Acta of Bioengineering and Biomechanics 11(3):11-18 (2009).
PCT/US10/42355 Search Report mailed Sep. 2, 2010.
PCT/US10/28265 Search Report and Written Opinion mailed Dec. 13, 2010.
U.S. Appl. No. 11/158,724 Office Action Mailed Sep. 17, 2009.
Akoh et al., "One-Stage Synthesis of Raffinose Fatty Acid Polyesters." Journal Food Science (1987) 52:1570.
Albert et al., "Antibiotics for preventing recurrent urinary tract infection in non-pregnant women," Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2007243268 Exam Report dated Aug. 31, 2011.
AU2009251504 Exam Report dated Dec. 8, 2011.
AU2009270849 Exam Report dated Feb. 14, 2012.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.
CA 2615452 Office Action dated Dec. 19, 2012.
CA 2684482 Office Action Jul. 11, 2012.
CA 2684482 Office Action dated Nov. 10, 2011.
CA 2688314 Office Action dated Jun. 6, 2012.
CA 2730995 Office Action dated Sep. 26, 2012.
CA 2757276 Office Action dated Feb. 15, 2013.
CA 2756307 Office action dated Feb. 18, 2013.
CA 2756386 Office action dated Mar. 15, 2013.
CA 2613280 Office Action dated Oct. 2, 2012.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. Dec. 2005;26(35):7418-24.
Clair and Burks, "Thermoplastic/Melt-Processable Polyimides," NASA Conf. Pub. #2334 (1984), pp. 337-355.
CN 2006800258093 Office Action dated May 30, 2012.
CN 200880007308.1 Office Action dated Nov. 23, 2011.
CN 200880007308.1 Office Action dated Oct. 18, 2012.
CN 200880020515 Office Action dated Oct. 9, 2012.
CN 200880100102.3 Office Action dated Jun. 1, 2012.
CN 200980122691 Office Action dated Oct. 10, 2012.
CN 200780047425.6 Office action dated Aug. 3, 2012.
CN 200780047425.6 Office action dated Feb. 28, 2013.
CN 200980136432.2 Office action dated Jan. 14, 2013.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vase Biol 2008;28:820-826.
DERWENT-ACC-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides. "J. Polym Sci. 25:3373-3386 (1987).
Dzik-Jurasz, "Molecular imaging in vivo: an introduction," The British Journal of Radiology, 76:S98-S109 (2003).
EA 201001497 Office Action dated Feb. 11, 2013.
EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.

(56) References Cited

OTHER PUBLICATIONS

EP08733210.2 Search Report dated Oct. 23, 2012.
EP08756215.3 Search Report dated Oct. 5, 2011.
EP08756215.3 Search Report dated Jan. 28, 2013.
EP09805981.9 Office Action dated Feb. 13, 2013.
EP06787258.0 Office Action dated Mar. 15, 2013.
EP09755571.8 Search Report dated Apr. 9, 2013.
EP08705772.5 Search Report dated Feb. 20, 2013.
Ettmayer et al. Lessons learned from marketed and investigational prodrugs. J Med Chem. May 6, 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Hinds, WC. Aerosol Technology, Properties, Behavior and Measurement of Airborne Particles, Deparment of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FF-IR and FT-Raman Spectroscopy," J. of Structural Biology, 132, 112-122 (2000).
Jackson et al., "Characterization of perivascular poly(lactic-co-glycolic acid) films containing paclitaxel" Int. J. of Pharmaceutics, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://curhcartj.oxfordjournals.org/content/29/22/2733.full.pdf> entire document.
Jewell, et al., "Release of Plasmid DNA from Intravascular Stents Coated with Ultrathin Multilayered Polyelectrolyte Films" Biomacromolecules. 7: 2483-2491 (2006).
Johns, H.E, J.R.Cunningham, Thomas, Charles C., Publisher, "The Physics of Radiology," 1983, Springfield, IL, pp. 133-143.
Joner et al. "Site-specific targeting of nanoparticle prednisolone reduces in-stent restenosis in a rabbit model of established atheroma," Arterioscler Thromb Vase Biol. 2008;28:1960-1966.

Mei et al., "Local Delivery of Modified Paclitaxel-Loaded Poly(ε-caprolactone)/Pluronic F68 Nanoparticles for Long-Term Inhibition of Hyperplasia," Journal of Pharmaceutical Sciences, vol. 98, No. 6, Jun. 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011.
JP-2009-534823 Office Action dated Sep. 20, 2012.
JP-2009-534823 Office Action dated Feb. 21, 2012.
JP-2009-545647 Office Action dated Jun. 5, 2012.
JP-2010-504253 Office Action dated Dec. 12, 2011.
JP-2010-504253 Office Action dated Dec. 7, 2012.
JP-2011-518920 Office action dated Dec. 17, 2012.
JP-2012-503677 Office action dated Jan. 18, 2013.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., Cyclic Acetals of4,1',6',-Trichloro-4,1',6',-Trideoxy-Trideoxy-galacto-Sucrose and their Conversion into Methyl Ether Derivatives. Carb. ResCarb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
KR10-2008-7003756 Office Action dated Oct. 30, 2012.
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Lee et al., "Novel therapy for hearing loss: delivery of insulin-like growth factor 1 to the cochlea using gelatin hydrogel," Otol. Neurotol. 28(7):976-81 (2007).
Lehmann et al, "Drug treatment of nonviral sexually transmitted diseases: specific issues in adolescents," Pediatr Drugs 3(7):481-494 (2001.
Mahoney et al., "Three-Dimensional Compositional Analysis of Drug Eluting Stent Coatings Using Cluster Secondary Ion mass Spectrometry," Anal. Chem. , 80, 624-632 (2008).
Mario, C.D. et al., "Drug-Eluting Bioabsorbable Magnesium Stent," J. Interventional Cardiology 16(6):391-395 (2004).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67 A, No. 3, pp. 981-993 (2003).
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 2008, 12-13.

(56) References Cited

OTHER PUBLICATIONS

Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et at., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
PCT/US08/50536 International Search Report mailed Jun. 2, 2008.
PCT/US08/60671 International Search Report mailed Sep. 5, 2008.
PCT/US08/64732 International Search Report mailed Sep. 4, 2008.
PCT/US09/41045 International Search Report mailed Aug. 11, 2009.
PCT/US09/50883 International Search Report mailed Nov. 17, 2009.
PCT/US12/46545 International Search Report mailed Nov. 20, 2012.
PCT/US12/50408 International Search Report mailed Oct. 19, 2012.
PCT/US2012/040040 International Search Report mailed Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 2001; 9:1-9.97.
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 2008;1;209-216.
Sahajanand Medical Technologies (Supralimus Core; Jul. 6, 2008).
Schetsky, L. McDonald, "Shape Memory Alloys", Encyclopedia of Chemical Technology (3d Ed), John Wiley & Sons 1982, vol. 20 pp. 726-736.
Schmidt et al., "New aspects of in vitro testing of arterial stents based on the new European standard," EN 14299, [online] (2009), [retrieved on Mar. 10, 2010] http://www.lib0cv.de/pl/pdf/EN14299. pdf (2009).
Schmidt et al., "Trackability, Crossability, and Pushability of Coronary Stent Systems—An Experimental Approach," Biomed Techn 47 (2002), Erg. 1, S. 124-126.

Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
SG201007602-4 Examination Report dated Feb. 13, 2013.
Simpson et al., "Hyaluronan and hyaluronidase in genitourinary tumors." Front Biosci. 13:5664-5680.
Smith et al., "Mitomycin C and the endoscopic treatment of laryngotracheal stenosis: are two applications better than one?" Laryngoscope 119(2):272-283 (2009).
Szabadits et al., "Flexibility and trackability of laser cut coronary stent systems," Acta of Bioengineering and Biomechanics 11(3): 11-18 (2009).
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Merriam-Webster Online Dictionary, obtained onlie at: http://www.merriam-webster.com/dictionary/derivative, downloaded 07 Jul. 5, 2008.
U.S. Appl. No. 11/158,724 Office Action Mailed Sep. 8, 2008.
U.S. Appl. No. 11/995,685 Office Action Mailed Aug. 20, 2010.
U.S. Appl. No. 11/995,685 Office Action Mailed Nov. 24, 2009.
U.S. Appl. No. 11/995,687 Office Action Mailed Sep. 28, 2011.
U.S. Appl. No. 12/298,459 Office Action Mailed Aug. 10, 2011.
U.S. Appl. No. 12/298,459 Office Action mailed Apr. 6, 2012.
U.S. Appl. No. 12/426,198 Office Action Mailed Feb. 6, 2012.
U.S. Appl. No. 12/426,198 Office Action Mailed Mar. 23, 2011.
U.S. Appl. No. 12/443,959 Office Action Mailed Dec. 13, 2012.
U.S. Appl. No. 12/443,959 Office Action mailed Feb. 15, 2012.
U.S. Appl. No. 12/504,597 Final Office Action Mailed Oct. 3, 2012.
U.S. Appl. No. 12/504,597 Office Action Mailed Dec. 5, 2011.
U.S. Appl. No. 12/522,379 Office Action Mailed Dec. 26, 2012.
U.S. Appl. No. 12/595,848 Office Action Mailed Jan. 13, 2012.
U.S. Appl. No. 12/601,101 Office Action Mailed Dec. 27, 2012.
U.S. Appl. No. 12/601,101 Office Action Mailed Mar. 27, 2012.
U.S. Appl. No. 12/648,106 Final Office Action Mailed Sep. 25, 2012.
U.S. Appl. No. 12/648,106 Office Action Mailed Jan. 30, 2012.
U.S. Appl. No. 12/729,156 Final Office Action Mailed Oct. 16, 2012.
U.S. Appl. No. 12/729,156 Office Action Mailed Feb. 1, 2012.
U.S. Appl. No. 12/729,580 Office Action Mailed Apr. 10, 2012.
U.S. Appl. No. 12/729,580 Office Action Mailed Jan. 22, 2013.
U.S. Appl. No. 12/729,603 Final Office Action Mailed Oct. 10, 2012.
U.S. Appl. No. 12/729,603 Office Action Mailed Mar. 27, 2012.
U.S. Appl. No. 12/751,902 Office Action Mailed Jul. 13, 2012.
U.S. Appl. No. 12/595,848 Office Action Mailed Mar. 15, 2013.
U.S. Appl. No. 12/738,411 Final Office action Mailed Apr. 11, 2013.
U.S. Appl. No. 12/762,007 Office action Mailed Feb. 11, 2013.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," Small 2010, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).

(56) References Cited

OTHER PUBLICATIONS

Wermuth, CG Similarity in drugs: reflections on analogue design. Drug Discov Today. Apr. 2006;11(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.
PCT/US10/28253 Search Report and Written Opinion mailed Dec. 6, 2010.
PCT/US10/28265 Search Report and Written Opinion mailed Dec. 3, 2010.
PCT/US10/28195 Search Report and Written Opinion mailed Jan. 21, 2011.
PCT/US10/31470 Search Report and Written Opinion mailed Jan. 28, 2011.
PCT/US10/29494 Search Report and Written Opinion mailed Feb. 7, 2011.
PCT/US11/22623 Search Report and Written Opinion mailed Mar. 28, 2011.
PCT/US2011/044263 International Search Report, International Preliminary Report on Patentability and Written Opinion dated Feb. 9, 2012.
PCT/US2007/82775 International Preliminary Report on Patentablity dated Apr. 28, 2009.
PCT/US09/69603 International Search Report mailed Nov. 5, 2010.
PCT/US09/50883 International Preliminary Report on Patentability dated Jan. 18, 2011.
PCT/US10/28253 International Preliminary Report on Patentability dated Sep. 27, 2011.
PCT/US12/33367 International Search Report mailed Aug. 1, 2012.
PCT/US10/42355 International Preliminary Report on Patentability dated Jan. 17, 2012.
PCT/US2011/67921 Search Report and Written Opinion mailed Jun. 22, 2012.
PCT/US2011/051092 International Preliminary Report on Patentability dated Mar. 21, 2013.
PCT/US10/28195 International Preliminary Report on Patentability dated Oct. 6, 2011.
AU2006270221 Exam Report dated Apr. 6, 2010.
AU2011232760 Exam Report dated Apr. 10, 2013.
AU2012203203 Exam Report dated Apr. 12, 2013.
AU2007243268 Exam Report dated May. 15, 2013.
AU2012203577 Exam Report dated Jun. 7, 2013.
AU2011256902 Exam Report dated Jun. 13, 2013.
CA 2759015 Office action dated Apr. 8, 2013.
CA 2756388 Office Action dated Apr. 11, 2013.
CA 2730995 Office action dated May 29, 2013.
CA 2650590 Office action dated Jul. 23, 2013.
Chlopek et al. "The influence of carbon fibres on the resorption time and mechanical properties of the lactide-glycolide co-polymer." J. Biomater. Sci. Polymer Edn, vol. 18, No. 11, pp. 1355-1368 (2007).
CN 200880100102.3 Office Action dated Apr. 11, 2013.
CN 200880007308.1 Office Action dated Jul. 3, 2013.
CN 200880020515 Office Action dated Jul. 22, 2013.
Cohen, et al. "Sintering Technique for the Preparation of Polymer Matrices fro the Controlled Release of Macromolecules." Journal of Pharmaceutical Sciences, vol. 73, No. 8, 1984, p. 1034-1037.
Domingo, C. et al., "Precipication of ultrafine organic crystals from the rapid expansion of supercritical solutions over a capillary and a frit nozzle," J. Supercritical Fluids 10:39-55 (1997).
EP07756094.4 Office action dated May 29, 2013.
EP08733210.2 Office action dated Jul. 16, 2013.
EP11769546.0 Search Report dated Sep. 19, 2013.
IN-368/DELNP/2008 Exam Report dated Oct. 17, 2011.
IL-208648 Official Notification dated Feb. 9, 2012.
JP-2009-534823 Office Action dated Apr. 23, 2013.
JP-2011-505248 Office action dated Jun. 4, 2013.
JP-2010-510441 Office action dated May 7, 2013.
JP-2009-545647 Office Action dated May 14, 2013.
Koh et al. "A novel nanostructured poly(lactic-co-glycolic-acid)-multi-walled carbon nantube composite for blood-contacting applications: Thrombogenicity studies." Acta Biomaterialia 5 (2009): 3411-3422.
KR10-2008-7003756 Office Action dated Sep. 23, 2013.
NZ 588549 Examination Report dated Mar. 28, 2011.
Schmidt et al., "A Comparison of the Mechanical Performance Characteristics of Seven Drug-Eluting Stent Systems," Catheterization and Cariovascular Interventions 73:350-360 (2009).
Shekunov et al. "Crystallization Processes in Pharmaceutical Technology and Drug Delivery Design." Journal of Crystal Growth 211 (2000), pp. 122-136.
U.S. Appl. No 13/605,904 Office Action Mailed Nov. 27, 2012.
U.S. Appl. No. 13/384,216 Office action Mailed Apr. 24, 2013.
U.S. Appl. No. 13/340,472 Office action Mailed Apr. 26, 2013.
U.S. Appl. No. 12/729,156 Office action Mailed May 8, 2013.
U.S. Appl. No. 13/014,632 Office action Mailed May 8, 2013.
U.S. Appl. No. 13/086,335 Office action Mailed May 22, 2013.
U.S. Appl. No. 11/158/724 Office action Mailed May 23, 2013.
U.S. Appl. No. 12/601,101 Office action May 22, 2013.
U.S. Appl. No. 12/298,459 Office Action Mailed May 31, 2013.
U.S. Appl. No. 13/229,473 Office Action Mailed Jun. 17, 2013.
U.S. Appl. No. 13/605,904 Office Action Mailed Jun. 28, 2013.
U.S. Appl. No. 11/877,591 Office Action Mailed Jul. 1, 2013.
U.S. Appl. No. 12/748,134 Office Action Mailed Jul. 18, 2013.
U.S. Appl. No. 12/738,411 Office action Mailed Aug. 21, 2013.
U.S. Appl. No. 12/522,379 Final Office Action Mailed Aug. 28, 2013.
U.S. Appl. No. 12/648,106 Office Action Mailed Sep. 18, 2013.
Wu et al., "Study on the preparation and characterization of biodegradable polylactid/multi-walled carbon nanotubes nanocomposites," Polymer 48 (2007) 4449-4458.
PCT/US2011/29667 International Search Report and Written Opinion mailed Jun. 1, 2011.
PCT/US2011/67921 International Preliminary Report on Patentability dated Jul. 11, 2013.
Abreu Filho et al., "Influence of metal alloy and the profile of coronary stents in patients with multivessel coronary disease," Clinics 2011;66(6):985-989.
CA 2757276 Office Action dated Feb. 5, 2014.
CA 2794704 Office action dated Feb. 7, 2014.
CA 2615452 Office Action dated Oct. 8, 2013.
CA 2613280 Office action dated Dec. 10, 2013.
CA 2667228 Office action dated Jan. 22, 2014.
CA 2679712 Office action dated Feb. 24, 2014.
CA 2667228 office action dated May 7, 2013.
CA 2730995 Office Action dated Feb. 20, 2014.
CA 2756386 Office action dated Oct. 24, 2013.
CA 2805631 Office Action dated Jan. 17, 2014.
CN 200880007308.1 Office Action dated Jan. 2, 2014.
CN 200880100102.3 Office Action dated Dec. 11, 2013.
CN 200980136432.2 Office action dated Nov. 4, 2013.
CN 201080024973.9 Office action dated Dec. 20, 2013.
Colombo et al. "Selection of Coronary Stents," Journal of the American College of Cardiology, vol. 40, No. 6, 2002, p. 1021-1033.
EA 200901254 Office Action dated Jul. 29, 2013.
EA 201001497 Office Action dated Jul. 29, 2013.
EP07756094.4 Office Action dated Jan. 21, 2014.
EP08705772.5 Office Action dated Oct. 30, 2013.
EP09755571.8 Office Action dated Dec. 13, 2013.
EP09798764.8 Search Report dated Sep. 30, 2013.
EP10756676.2Search Report dated Jan. 31, 2014.
EP10756696.0 Search Report dated Oct. 10, 2013.
EP10764884.2 Search Report dated Oct. 28, 2013.
EP10765295.0 Search Report dated Oct. 17, 2013.
EP10800642.0 Search Report dated Mar. 19, 2004.
IL-201550 Official Notification dated Dec. 8, 2013.
IN-6884DEFNP2009 Office Action dated Oct. 31, 2013.
JP-2011-518920 Office action dated Oct. 23, 2013.
JP-2012-503677 Office action dated Nov. 1, 2013.
JP-2012-151964 Office Action dated Dec. 10, 2013.
KR10-2013-7031237 Office action dated Mar. 17, 2014.

(56) References Cited

OTHER PUBLICATIONS

Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
MX/a/2010/01148 Office action dated Feb. 11, 2014.
PCT/US06/24221 International Preliminary Report on Patentability dated Dec. 24, 2007.
PCT/US06/27321 International Preliminary Report on Patentability dated Jan. 16, 2008.
PCT/US06/27322 International Preliminary Report on Patentability dated Jan. 16, 2008.
PCT/US07/10227 International Preliminary Report on Patentability dated Oct. 28, 2008.
PCT/US07/80213 International Preliminary Report on Patentability dated Apr. 7, 2009.
PCT/US08/11852 International Preliminary Report on Patentability dated Apr. 20, 2010.
PCT/US08/50536 International Preliminary Report on Patentability dated Jul. 14, 2009.
PCT/US08/60671 International Preliminary Report on Patentability dated Oct. 20, 2009.
PCT/US08/64732 International Preliminary Report on Patentability dated Dec. 1, 2009.
PCT/US09/41045 International Preliminary Report on Patentability dated Oct. 19, 2010.
PCT/US09/69603 International Preliminary Report on Patentability dated Jun. 29, 2011.
PCT/US10/28265 International Report on Patentability dated Sep. 27, 2011.
PCT/US10/29494 International Preliminary Report on Patentability dated Oct. 4, 2011.
PCT/US10/31470 International Preliminary Report on Patentability dated Oct. 18, 2011.
PCT/US11/032371 International Report on Patentability dated Oct. 16, 2012.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US12/33367 International Preliminary Report on Patentability dated Oct. 15, 2013.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
U.S. Appl. No. 11/158,724 Office action Mailed Dec. 31, 2013.
U.S. Appl. No. 12/426,198 Office Action mailed Feb. 7, 2014.
U.S. Appl. No. 12/504,597 Office Action Mailed Apr. 1, 2014.
U.S. Appl. No. 12/595,848 Office Action Mailed Oct. 22, 2013.
U.S. Appl. No. 12/601,101 Office Action mailed Feb. 13, 2014.
U.S. Appl. No. 12/729,156 Office Action Mailed Feb. 13, 2014.
U.S. Appl. No. 12/729,580 Final Action dated Nov. 14, 2013.
U.S. Appl. No. 12/738,411 Office Action mailed Feb. 6, 2014.
U.S. Appl. No. 12/751,902 Office Action Mailed Dec. 19, 2013.
U.S. Appl. No. 12/762,007 Final Office action Mailed Oct. 22, 2013.
U.S. Appl. No. 13/014,632 Office action Mailed Jan. 10, 2014.
U.S. Appl. No. 13/340,472 Office action Mailed Jan. 15, 2014.
U.S. Appl. No. 13/384,216 Final Action dated Nov. 6, 2013.
U.S. Appl. No. 13/445,723 Office action mailed Mar. 14, 2014.
Zilberman et al., Drug-Eluting bioresorbable stents for various applications, Annu Rev Biomed Eng., 2006;8:158-180.
CA 2756307 Office action dated Mar. 24, 2014.
CA 2756388 Office Action dated Apr. 14, 2014.
CA 2756386 Office action dated May 16, 2014.
CA 2823355 Office action dated Apr. 14, 2014.
CN 200880020515 Office Action dated Apr. 15, 2014.
CN 200980136432.2 Office action dated Jul. 3, 2014.
EP11772624.0 Search Report dated Jun. 5, 2014.
EP09798764.8 Office action dated Jun. 30, 2014.
ID-W00201003529 Office action dated Apr. 28, 2014.
IN-7740/DELNP/2009 Office Action dated Jul. 29, 2014.
JP-2009-545647 Office Action dated Apr. 22, 2014.
JP-2013-024508 Office Action dated Apr. 24, 2014.
PCT/US2014/025017 International Search Report and Written Opinion dated Jul. 7, 2014.
Putkisto, K. et al. "Polymer Coating of Paper Using Dry Surface Treatment—Coating Structure and Performance", ePlace newsletter, Apr. 12, 2004, vol. 1, No. 8, pp. 1-20.
U.S. Appl. No. 11/158,724 Office Action Mailed Jun. 25, 2014.
U.S. Appl. No. 12/522,379 Office Action Mailed Apr. 8, 2014.
U.S. Appl. No. 12/729,603 Office Action Mailed Jun. 25, 2014.
U.S. Appl. No. 12/738,411 Office Action mailed May 30, 2014.
U.S. Appl. No. 12/762,007 Final Office action Mailed Apr. 30, 2014.
U.S. Appl. No. 13/086,335 Office action Mailed Apr. 4, 2014.
U.S. Appl. No. 13/090,525 Office action mailed Apr. 11, 2014.
U.S. Appl. No. 11/995,685 Office Action Mailed Jun. 18, 2014.
CN 201210206265.8 Office Action dated Sep. 15, 2014.

\* cited by examiner

Expanded Configuration A

Collapsed Configuration A

Expanded Configuration B

Collapsed Configuration B

Expanded Configuration C

Collapsed Configuration C

Expanded, Configuration C with 5

Collapsed, Configuration C with 5

Expanded, Configuration D

Collapsed, Configuration D

Configuration E

Expanded Configuration F

Collapsed Configuration F

Configuration G

Configuration H

Configuration I

Configuration I- top view

Configuration J

Configuration K

Configuration L

Configuration M

Configuration N

Configuration O

Configuration P

Configuration Q

Configuration R

Configuration S

Configuration T

Configuration U

HOLDER FOR ELECTRICALLY CHARGING A SUBSTRATE DURING COATING

CROSS-REFERENCE

This application claims the benefit of U.S. Provisional Application No. 60/862,592, filed Oct. 23, 2006, which application is incorporated herein by reference.

BACKGROUND OF THE INVENTION

It is often beneficial to provide coatings onto substrates, such that the surfaces of such substrates have desired properties or effects.

For example, it is useful to coat biomedical implants to provide for the localized delivery of pharmaceutical or biological agents to target specific locations within the body, for therapeutic or prophylactic benefit. One area of particular interest is drug eluting stents (DES) that has recently been reviewed by Ong and Serruys in Nat. Clin. Pract. Cardiovasc. Med., (December 2005), Vol 2, No 12, 647. Typically such pharmaceutical or biological agents are co-deposited with a polymer. Such localized delivery of these agents avoids the problems of systemic administration, which may be accompanied by unwanted effects on other parts of the body, or because administration to the afflicted body part requires a high concentration of pharmaceutical or biological agent that may not be achievable by systemic administration. The coating may provide for controlled release, including long-term or sustained release, of a pharmaceutical or biological agent. Additionally, biomedical implants may be coated with materials to provide beneficial surface properties, such as enhanced biocompatibility or lubriciousness.

Conventional solvent-based spray coating processes are hampered by inefficiencies related to collection of the coating constituents onto the substrate and the consistency of the final coating. As the size of the substrate decreases, and as the mechanical complexity increases, it grows increasingly difficult to uniformly coat all surfaces of a substrate.

A cost-effective method for depositing inert polymers and pharmaceutical or biological agents onto a substrate, where the collection process is efficient, the coating produced is conformal, substantially defect-free and uniform, the composition of the coating can be regulated and the morphology and/or secondary structure of the pharmaceutical or biological agents can be controlled is described in PCT/US 06/027,321, incorporated herein by reference in its entirety. The method permits structural and morphological preservation of the agents deposited during the coating process. The method as described in PCT/U.S. 06/027,321 contemplates electrically charging the stent and creating an electrical field around the stent and stent holder during the coating method.

What is needed, therefore, is a stent holder which mounts and electrically charges a stent.

SUMMARY OF THE INVENTION

The present invention relates to a holder for mounting and electrically charging a stent during a coating process, an assembly for coupling, supporting, and electrically charging the stent holder, a chamber for controlling the electrical field around the stent and providing a platform for coating a stent, and a method of coating a stent using the electrically charged holder, electrically charged assembly, and chamber.

In one aspect, the invention provides a stent holder for removably holding a stent during a coating process wherein the stent holder charges the stent during the coating process. In one embodiment the holder forms an electrical field around the stent. In another embodiment the holder comprises a mask for masking at least a part of the stent. In another embodiment the holder comprising a support interfacing portion for interfacing with a support, wherein the support supports and electrically charges the support interfacing portion. In another embodiment, the stent holder comprises a stent mounting portion that electrically charges the stent. In another embodiment the stent mounting portion the stent mounting portion has a configuration whereby the stent slides over an elliptical portion of the stent holder. In another embodiment the stent mounting portion has a collapsed and an expanded state for minimizing coating damage during mounting or removal of the stent. In another embodiment the stent sits on an electrically chargeable section of the stent mounting portion. In another embodiment the stent mounting portion comprises a spring section. In another embodiment, the stent mounting portion comprises threads winding around a central axis. In another embodiment the threads are non-conductive. In another embodiment the threads are electrically chargeable. In another embodiment the holder further comprises a member for manipulating the electrical field around the stent. In other embodiments, the holder is in varied configurations capable of mounting and electrically charging the stent and creating an electrical field around the stent.

In one aspect, the invention provides an assembly comprising: at least one stent holder for removably holding a stent during a coating process wherein the stent holder charges the stent during the coating process; and a support for supporting the at least one stent holder, wherein the support electrically charges the stent holder. In one embodiment, the stent holder of the assembly comprises a support interfacing portion for interfacing with the support, wherein the support supports and electrically charges the support interfacing portion. In another embodiment, the support of the assembly comprises at least one coupling portion for electrically coupling to the support interfacing portion of the stent holder. In another embodiment, the support of the assembly comprises a charging portion connected to an electrical source. In other embodiments, the coupling portion is in varied configurations capable of electrically charging and supporting the holder.

In one aspect, the invention provides a chamber for a stent coating process wherein the chamber comprises:
 a base comprising a first hole;
 an assembly comprising: at least one stent holder for removably holding a stent during a coating process wherein the stent holder charges the stent during the coating process, and a support for supporting the at least one stent holder, wherein the support electrically charges the stent holder; and
 a coating nozzle for coating the stent held by the assembly,
 wherein the assembly sits on the base, wherein the first base hole provides the coating nozzle access to the chamber for coating the stent, and wherein the coating nozzle is removably fitted in the first base hole. In one embodiment, the chamber further comprises at least one grounded member connected to a ground source. In another embodiment, a grounded member is removably fitted in the first or a second base hole. In another embodiment, the chamber further comprises a purge nozzle for purging the chamber, wherein the purge nozzle is fitted in the first, the second, or a third base hole. In another embodiment, the chamber further comprises an insulating stand for insulating the base from the electrical charge of the assembly, wherein the assembly sits on the insulating stand, and the insulating stand sits on the base, and wherein the insulating stand has at least one hole aligning with the first, the second, the third, or a fourth base hole. In another embodiment, the chamber further comprises a cover that fits over the assembly and sits on the base. In another embodiment, the chamber further comprises at least one insulating grounded member outside the cover, wherein the insulating grounded member is connected to a ground source and removably sits on the base. In other embodiments, the cover is transparent, comprises an insulator material, and/or is disposable. In other embodiments, the base has non-conductive properties, and/or is a thermoformed plastic part. In another embodiment, the chamber comprises an electrical source connected to the support of the assembly. In another embodiment, the assembly of the chamber comprises a plurality of stent holders arranged in a circular configuration, and wherein the coating nozzle is positioned within the circular configuration formed by the holders.

In one aspect, the invention provides a method of coating a plurality of stents wherein the method comprises:
providing an assembly comprising a support and a plurality of stent holders, wherein the stent holders are arranged in a circular configuration, and wherein a coating nozzle is positioned within the circular configuration formed by the stent holders;
mounting the stents onto the stent holders;
electrically charging the stents by electrically charging the support which electrically charges the stent holder upon which the stents are mounted; and
exposing the electrically charged stents to coating particles from the coating nozzle wherein the electrically charged stents attract the coating particles and wherein the coating particles deposit on the stents while maintaining the stents stationary during coating.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments and the accompanying drawings of which:

DETAILED DESCRIPTION OF THE INVENTION

Figure 1A:
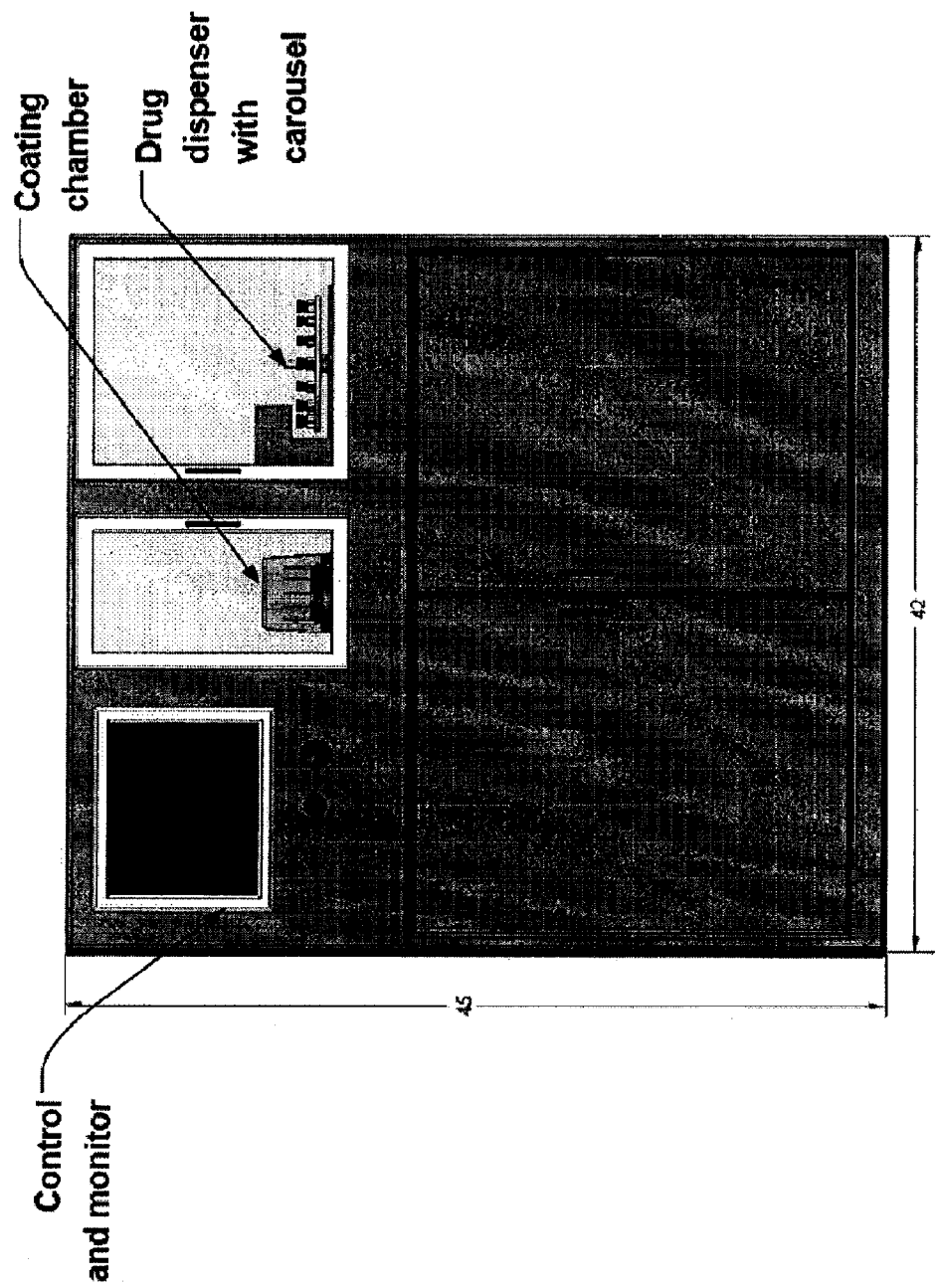
FIG. 1A to 1B shows a chamber of the invention within a coating system.
Figure 1B:
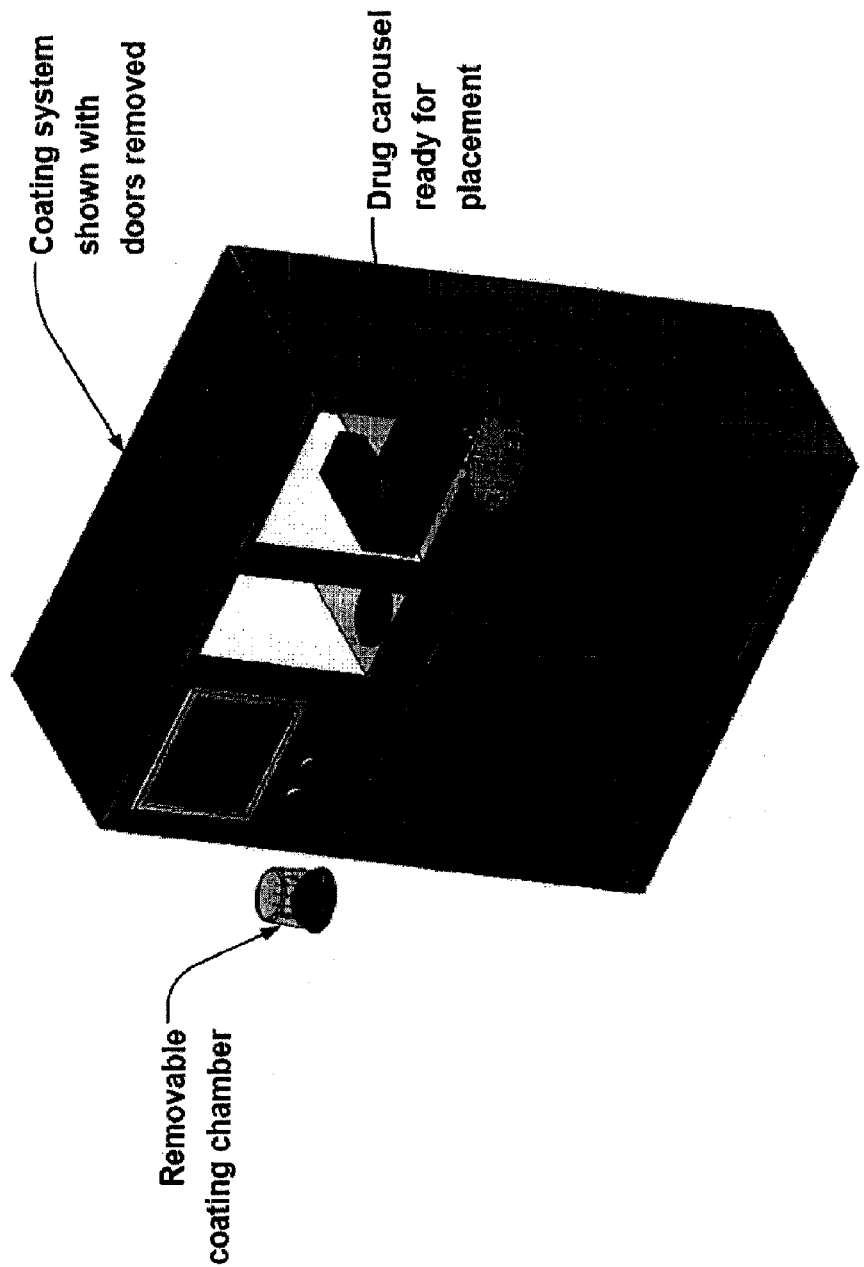
Figure 1C:
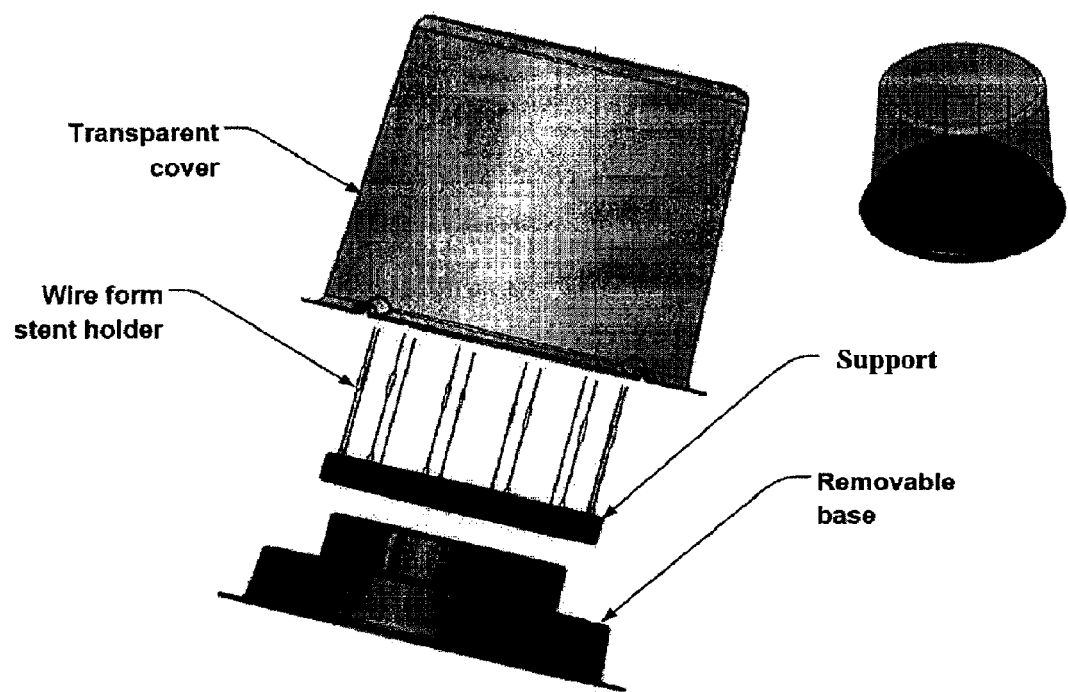
FIG. 1C shows a chamber of the invention.
Figure 2A:
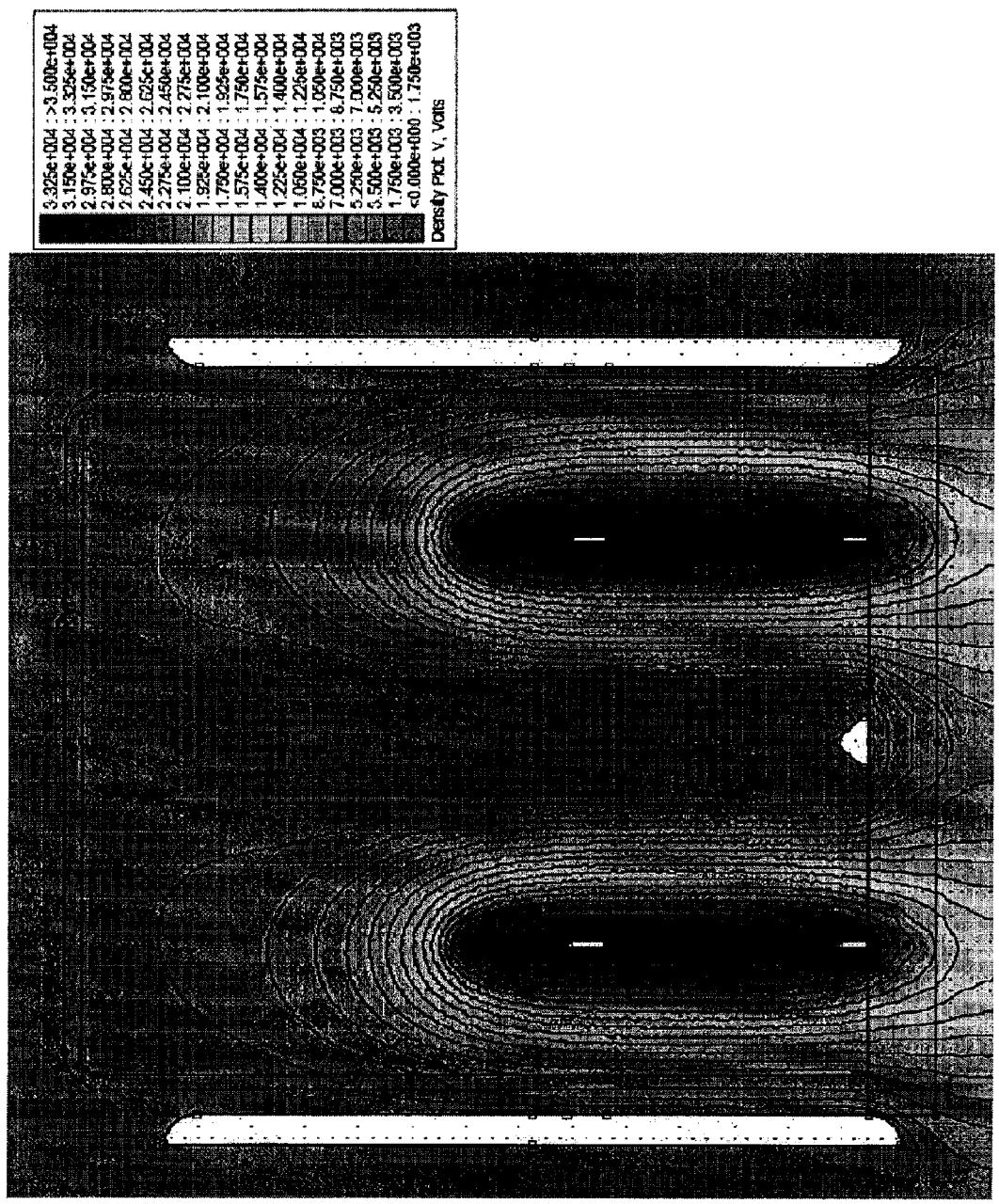
FIG. 2A shows an electrical field surrounding a stent and stent holder when charged within a chamber.
Figures 1C, 2B:
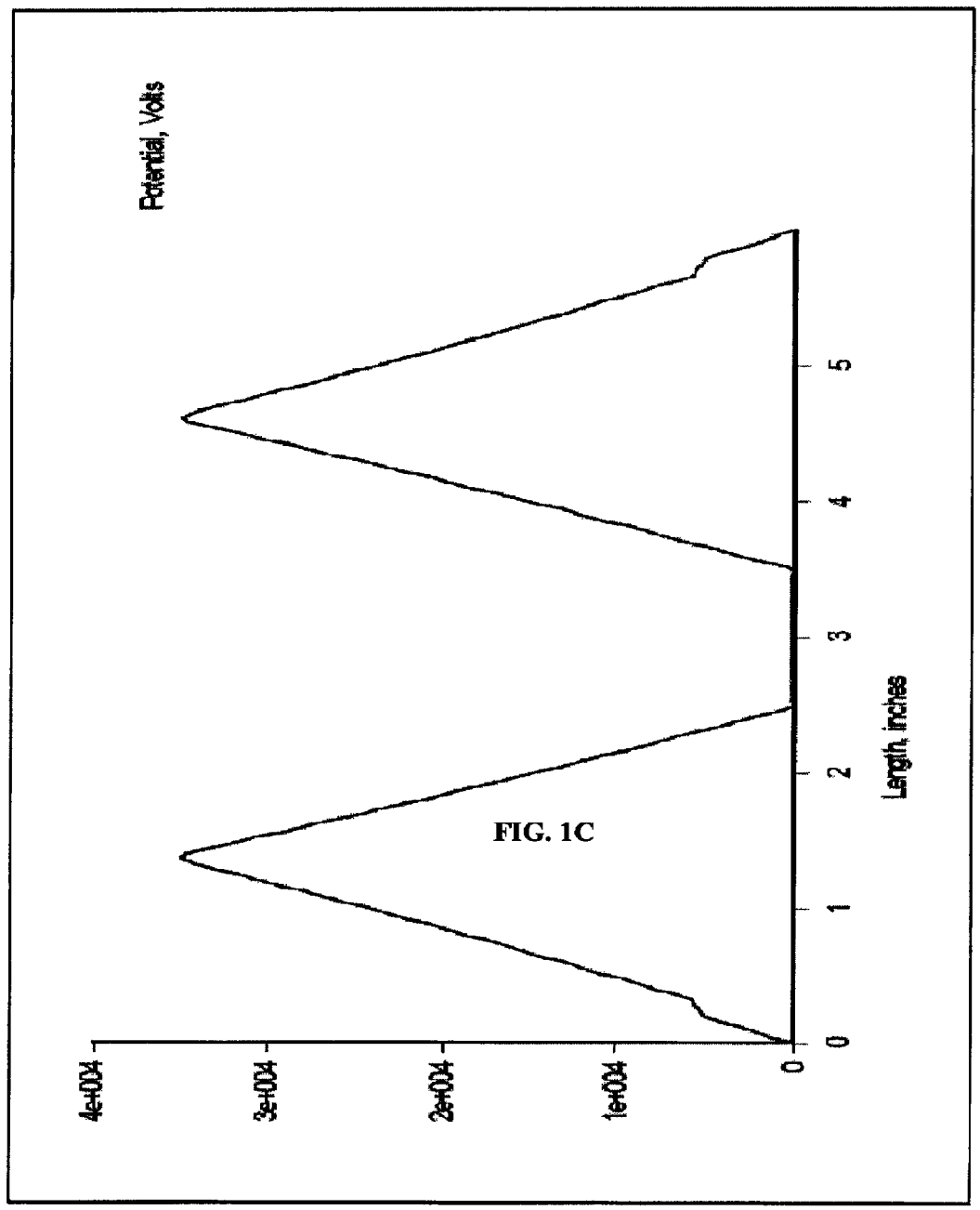
FIG. 2B shows the electric potential across the length of the chamber when the electrical field of FIG. 2A surrounds a stent and stent holder when charged within a chamber.
Figure 2C:
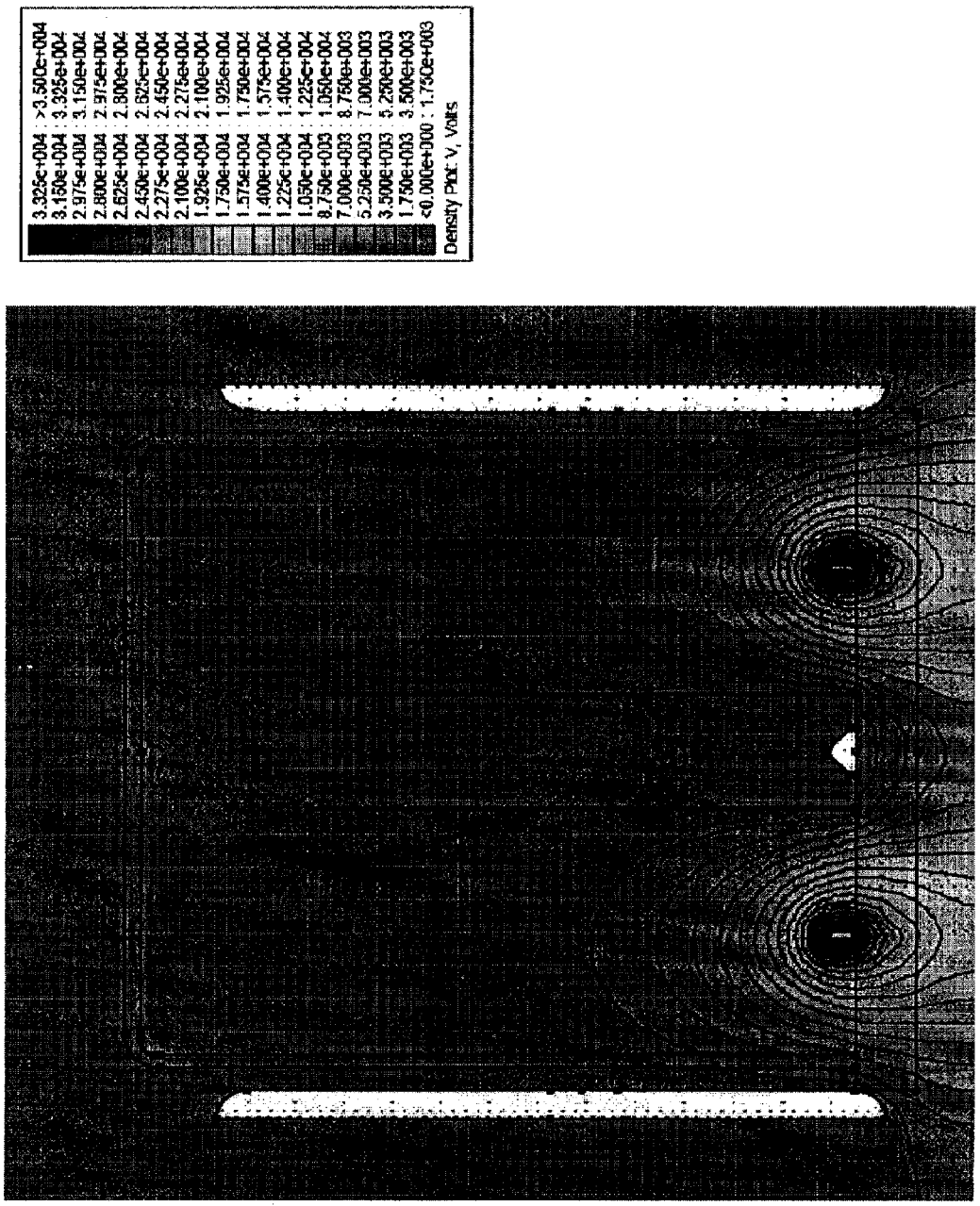
FIG. 2C shows an electrical field surrounding a stent and stent holder when charged within a chamber.
Figure 2D:
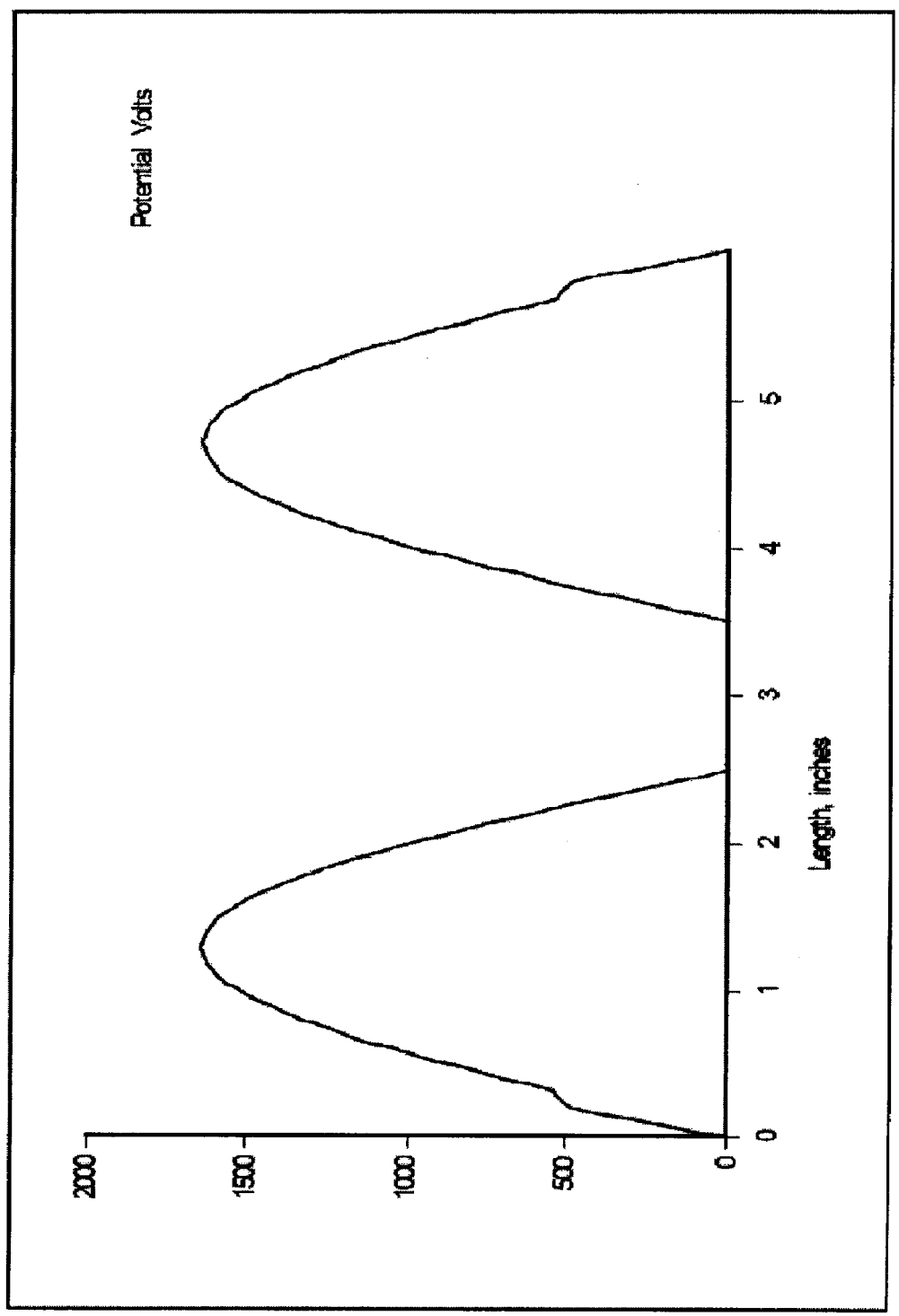
FIG. 2D shows the electric potential across the length of the chamber when the electrical field of FIG. 2C surrounds a stent and stent holder when charged within a chamber.
Figure 2E:
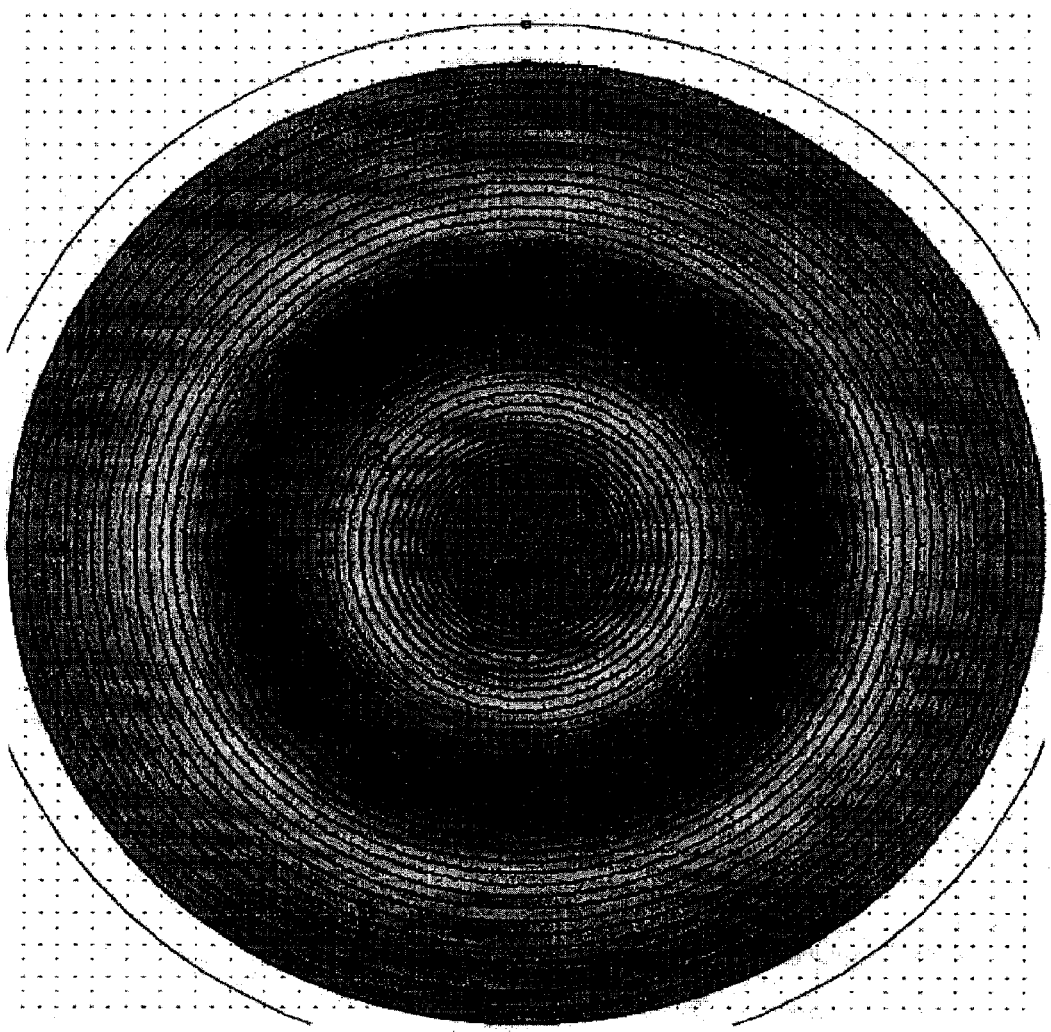
FIGS. 2E and 2F show top views of electrical fields surrounding a plurality of stents and stent holders when charged within a chamber.
Figure 2F:
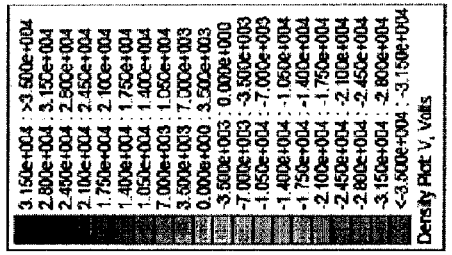
Figure 2F:
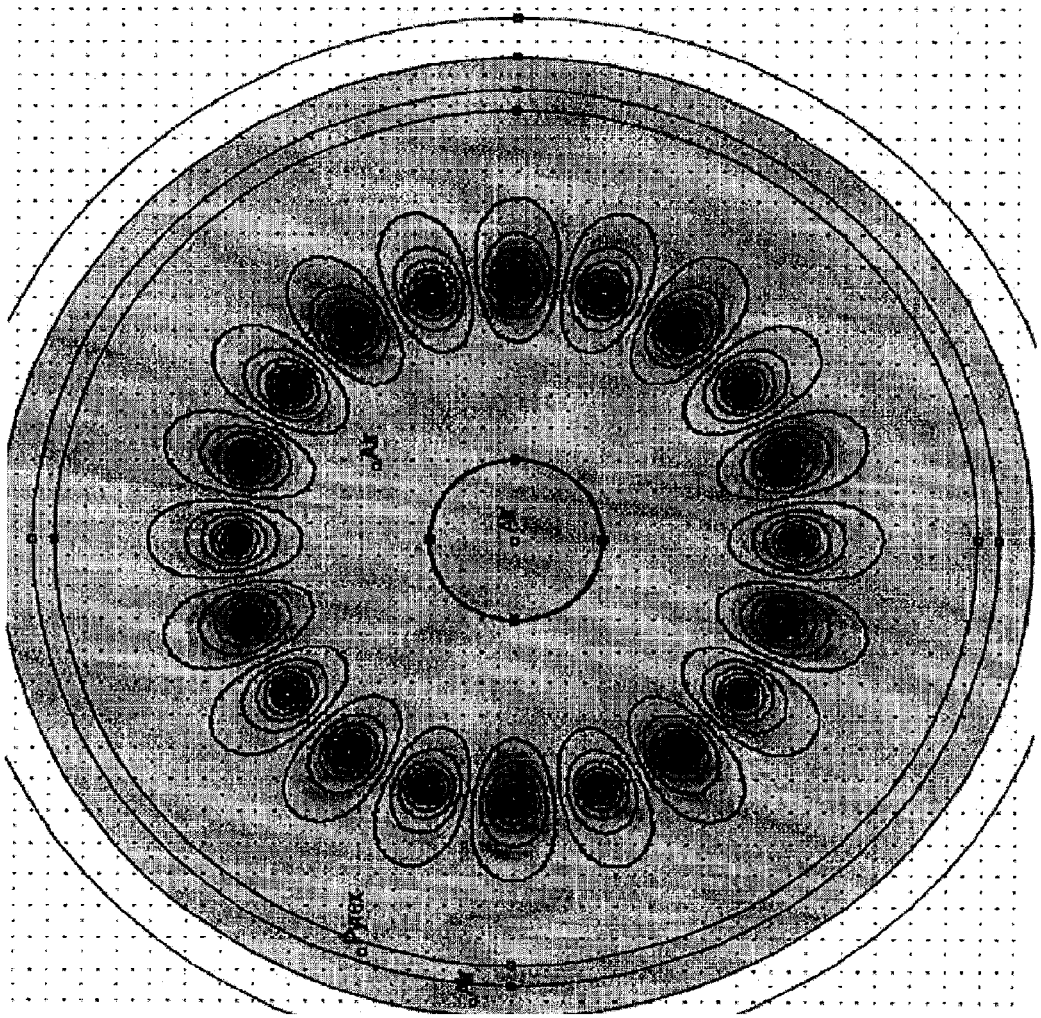

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to describe some particular embodiments of the invention, including the preferred embodiment, and not to exhaustively specify all permutations, combinations and variations thereof. The details of the embodiment may be changed without departing from the invention, which is defined by the claims.

Applicants specifically intend that all United States patent references cited herein be incorporated herein by reference in their entirety.

1. The Stent Holder

FIGS. 3A to 21 illustrate various stent holders for removably holding and electrically charging a stent during a coating process. The holders form electrical fields around the stents, embodiments of the fields shown in FIGS. 2A through 2F, which results in attraction of non-charged coating particles to the charged stent during the coating process. Any of the holders can be further configured with a conductive member in order to manipulate the electrical field around the stent. Examples of suitable conductive materials to conduct a charge from the holders to the stent include, but are not limited to, stainless steel and shape memory metal alloys, such as Nitinol (a Ni—Ti alloy).

FIGS. 3A to 6B show a stent (4) mounted on a stent holder (1) having a stent mounting portion (2), as shown, and a support interfacing portion (3). The stent mounting portion (2) has both an expanded and a collapsed state, and comprises at least two arms (30) upon which the stent (4) is mounted. In its expanded state, the stent mounting portion (2) has an outer distance, shown by double headed arrow (33), which is approximately equal to stent inner diameter, shown by double headed arrow (10). The stent mounting portion (2) in its expanded state exerts force on the inner surface of the stent in opposing directions, thereby holding the stent (4) in place, while minimizing stent deformation. When the first end (31) of the stent holder (1) and the second end (32) of the stent holder (1) are moved in opposite directions simultaneously, or the first end (31) is fixed and the second end (32) is moved away from the first end (31), the distance between the arms (30) reduces. This allows the stent (4) to be loaded onto the stent holder (1), or, alternatively, released from the stent holder (1) if already mounted by reducing contact between the stent (4) and the stent holder (1). The arms (30) are made of conductive material and conduct an electrical charge to the stent (4) when the arms (1) touch the stent (4).

Figure 3A:
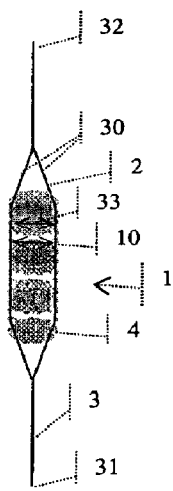
FIGS. 3A and 3B illustrate a stent holder in accordance with an embodiment of the invention and a stent, the stent holder having a stent mounting portion in Configuration A and a support interfacing portion.
Figure 3B:
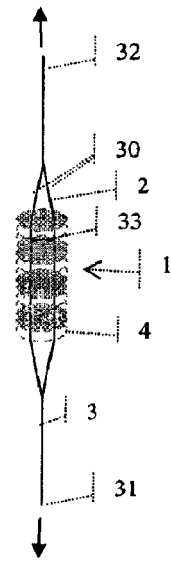

In the embodiment of FIGS. 3A and 3B, the stent mounting portion Configuration A has arms (30) that comprise an elliptical portion.

In another embodiment, the stent holder (1) has a stent mounting portion (2) in Configuration A, as shown in FIG. 3A, and a support interfacing portion (3), comprises at least two arms (30) upon which the stent (4) is mounted, without the stent mounting portion collapsed state of FIG. 3B. The stent (4) may be slid along the arms to be mounted and released from the stent holder (1).

Figure 4A:
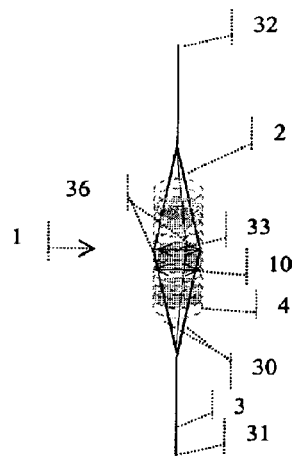
FIGS. 4A and 4B illustrate a stent holder in accordance with an embodiment of the invention and a stent, the stent holder having a stent mounting portion in Configuration B and a support interfacing portion.
Figure 4B:
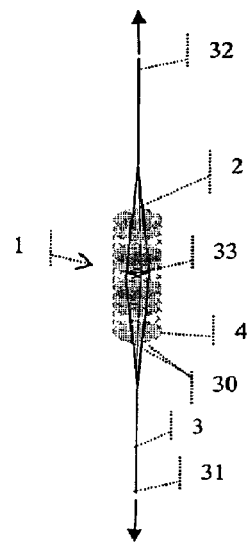

In the embodiment of FIGS. 4A and 4B, the stent mounting portion Configuration B has arms (30) extending from a central axis of the stent holder, making at least one bend, and returning to the central axis of the stent holder. In this embodiment, the number of contact points (36) between the stent (4) and the stent holder (1) is at least two.

Figure 5A:
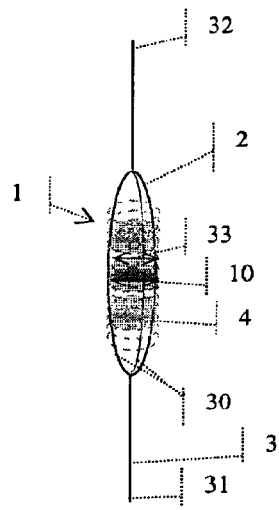
FIGS. 5A and 5B illustrate a stent holder in accordance with an embodiment of the invention and a stent, the stent holder having a stent mounting portion in Configuration C and a support interfacing portion.
Figure 5B:
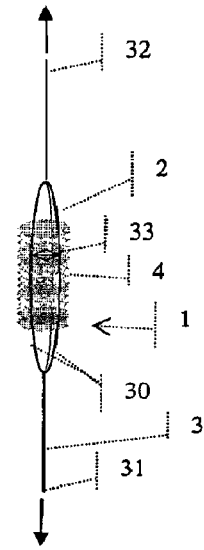

In the embodiment of FIGS. 5A and 5B, the stent mounting portion Configuration C has arms (30) extending from a central axis of the stent holder (1) and arcing to return to the central axis of the stent holder (1).

Figure 6A:
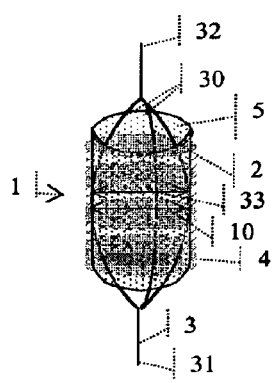
FIGS. 6A and 6B illustrate a stent holder in accordance with an embodiment of the invention, the stent holder having a mask and a stent mounting portion in Configuration C and a support interfacing portion.
Figure 6B:
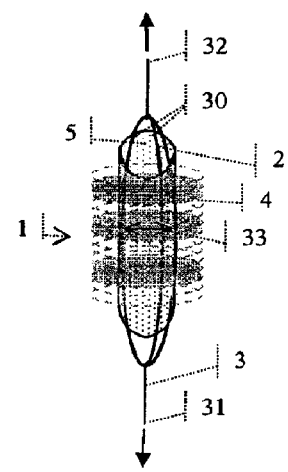

The embodiment of FIGS. 6A and 6B show a stent holder (1) having a stent mounting portion (2) in Configuration C and further comprising a mask (5). The mask (5) provides masking of the inner surface of the stent (4) so as to reduce and/or eliminate coating of the stent inner surface. Examples of suitable materials for the mask (5) include non-conductive materials, polymers, and/or non-stick materials such as polytetrafluoroethylene (e.g., TEFLON), and/or other non-conducting materials.

Figure 7A:
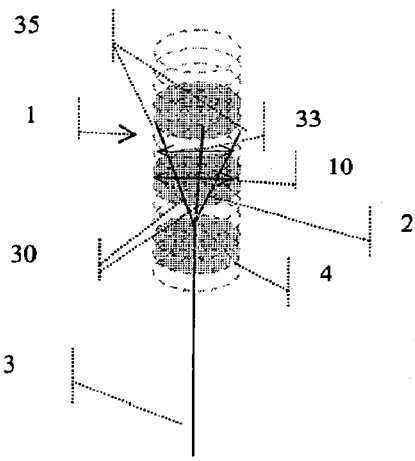
FIGS. 7A and 7B illustrate a stent holder in accordance with an embodiment of the invention and a stent, the stent holder having a stent mounting portion in Configuration D and a support interfacing portion.
Figure 7B:
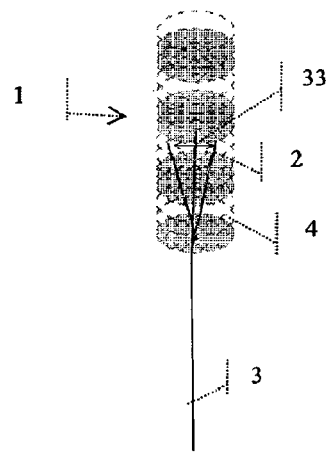

FIGS. 7A and 7B show a stent (4) mounted on a stent holder (1) having a stent mounting portion (2) in Configuration D, and a support interfacing portion (3). The stent mounting portion (2) Configuration D has both an expanded and a collapsed state, and comprises at least two arms (30) having free ends (35) upon which the stent (4) is mounted. In its expanded state, the stent mounting portion (2) has an outer distance, shown by double headed arrow (33), which is equal to or greater than the stent inner diameter, shown by double headed arrow (10). The stent mounting portion (2) in its expanded state exerts force on the inner surface of the stent in opposing directions and/or protrudes into a stent gap, thereby holding the stent (4) in place. When the arm free ends (35) are moved toward each other, the distance between the arm free ends (33) reduces. This allows the stent (4) to be loaded onto the stent holder (1), or, alternatively, released from the stent holder (1) if already mounted by reducing contact between the stent (4) and the stent holder (1). The arms (30) are made of conductive material and conduct an electrical charge to the stent (4) when the arms (30) touch the stent (4).

Figure 8:
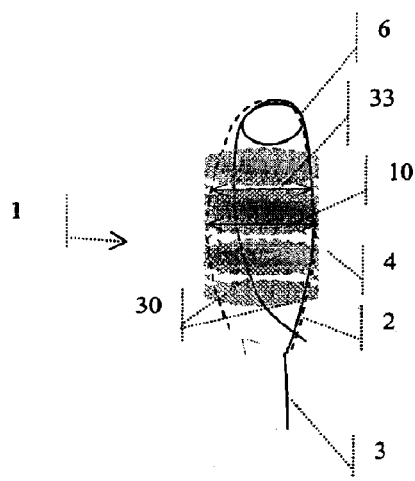
FIG. 8 illustrates a stent holder in accordance with an embodiment of the invention and a stent, the stent holder having a stent mounting portion in Configuration E, a support interfacing portion, and showing, in phantom lines, expansion of the stent mounting portion.

FIG. 8 shows a stent (4) mounted on a stent holder (1) having a stent mounting portion (2) in Configuration E, as shown, and a support interfacing portion (3). The stent mounting portion (2) comprises two arms (30) upon which the stent (4) is mounted. The stent mounting portion (2) in this embodiment can move or be moved between in an expanded state and a collapsed state by means of a spring section (6). The expanded state is shown in phantom lines. In its expanded state, the stent mounting portion (2) has an outer distance, shown by double headed arrow (33), which is equal to or greater than the stent inner diameter, shown by double headed arrow (10). The stent mounting portion (2) in its expanded state exerts forces on the inner surface of the stent in opposing directions, thereby holding the stent (4) in place. When the stent mounting portion distance (33) is reduced, manually or otherwise by moving the arms (30) toward each other, the stent (4) may be loaded onto the stent holder (1), or, alternatively, the stent (4) may be released from the stent holder (1) if already mounted, with reduced friction between the stent (4) and the stent holder (1). The arms (30) are made of conductive material and conduct an electrical charge to the stent (4) when the arms (1) touch the stent (4).

Figure 9A:
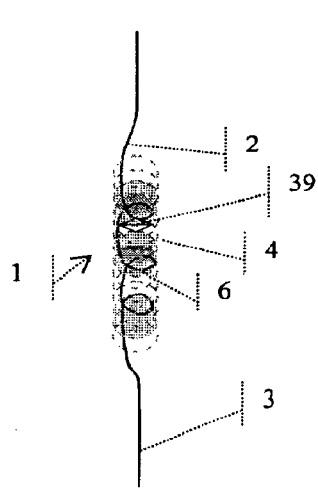
FIGS. 9A and 9B illustrate a stent holder in accordance with an embodiment of the invention and a stent, the stent holder having a stent mounting portion in Configuration F and a support interfacing portion.
Figure 9B:
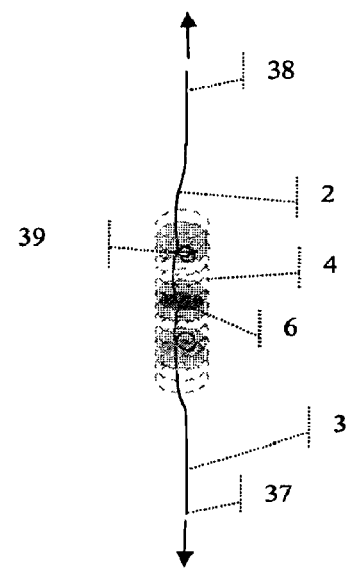

FIGS. 9A and 9B shows a stent (4) mounted on a stent holder (1) having a stent mounting portion (2) in Configuration F, as shown, and a support interfacing portion (3). The stent mounting portion (2) in this embodiment can move or be moved between in an expanded state and a collapsed state by means of a spring section (6). When the spring ends (37) and (38) are moved in opposite directions simultaneously, or the first end (37) of the spring is fixed and the second end (38) of the spring is moved away from the first end, or the opposite, the spring diameter (39) reduces. This allows the stent (4) to be loaded onto the stent holder (1), or, alternatively, released from the stent holder (1) if already mounted by reducing contact between the stent (4) and the stent holder (1). The spring ends (37) and (38) are made of conductive material, and conduct an electrical charge to the stent (4) when the arms (1) touch the stent (4).

Figure 10:
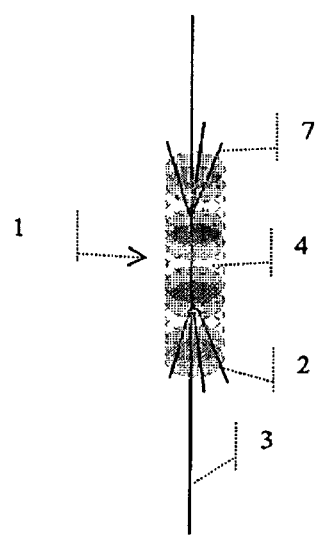
FIG. 10 illustrates a stent holder in accordance with an embodiment of the invention and a stent, the stent holder having a stent mounting portion in Configuration G and a support interfacing portion.

FIG. 10 shows a stent (4) mounted on a stent holder (1) having a stent mounting portion (2) in Configuration G, as shown, a support interfacing portion (3), and a removable cap (7). When the cap (7) is removed from the stent holder (1), a stent (4) can be mounted on the stent holder (1) by resting one end of the stent (4) on the stent mounting portion (2) of the stent holder (1), and replacing the cap (7) such that the opposite end of the stent (4) is also held by the cap (7) such that the stent central axis aligns with the central axis of the stent holder (1).

Figure 11:
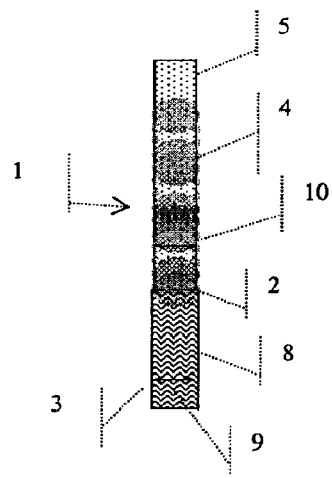
FIG. 11 illustrates a stent holder in accordance with an embodiment of the invention and a stent, the stent holder having a stent mounting portion in Configuration H and a support interfacing portion.

FIG. 11 shows a stent (4) mounted on a stent holder (1) having a stent mounting portion (2) in Configuration H, as shown, a support interfacing portion (3), a mask (5) for masking at least part of the stent inner surface, and an electrically chargeable section (8). In this embodiment, the electrically chargeable section (8) has a larger outer diameter, shown by double headed arrow (9), than the stent inner diameter, shown by double headed arrow (41), whereby, when mounted, the stent (4) sits on the electrically chargeable section (8). Examples of suitable materials for the mask (5) include non-conductive materials, polymers, and/or non-stick materials such as polytetrafluoroethylene (e.g., TEFLON).

In another embodiment, a variation of the embodiment of FIG. 1, the electrically chargeable section (8) has an outer diameter (9) that is approximately equivalent to the stent outer diameter (41), whereby, when mounted, the stent (4) extends over at least a part of the electrically chargeable section (8) and touches the electrically chargeable section (8).

Figure 12:
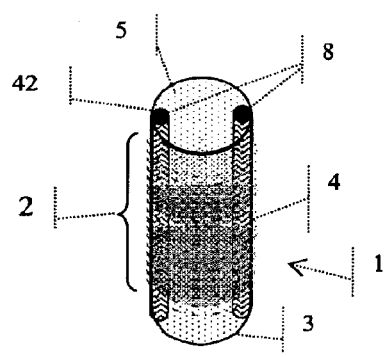
FIG. 12 illustrates a stent holder in accordance with an embodiment of the invention and a stent, the stent holder having a stent mounting portion in Configuration I and a support interfacing portion.

FIG. 12 shows a stent (4) mounted on a stent holder (1) having a stent mounting portion (2) in Configuration I, as shown, a support interfacing portion (3), a mask (5) for masking at least part of the stent inner surface, and an electrically chargeable section (8) comprising an electrically chargeable rod (42) extending the length of the stent (4). In this embodiment, the stent (4) extends over and touches the electrically chargeable rod (42). Examples of suitable materials for the mask (5) include non-conductive materials, polymers, and/or non-stick materials such as polytetrafluoroethylene (e.g., TEFLON).

Figure 13:
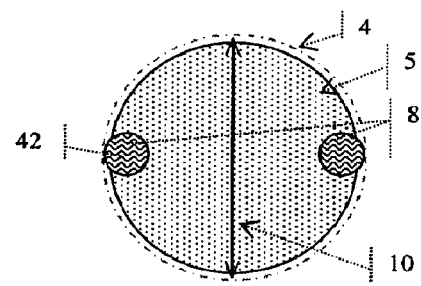
FIG. 13 illustrates a top view of the stent holder embodiment of FIG. 12 and stent.

FIG. 13 shows a top view of the stent holder (1) embodiment of FIG. 12 and stent (4).

Figure 14:
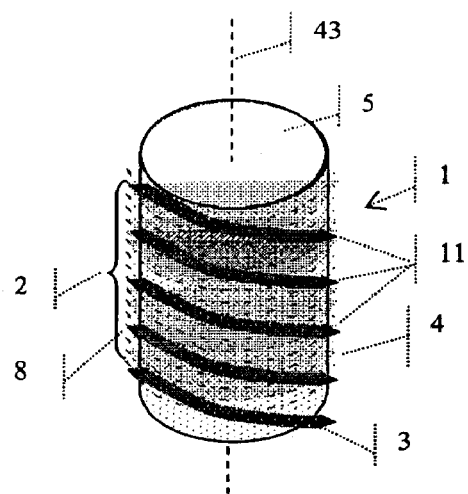
FIG. 14 illustrates a stent holder in accordance with an embodiment of the invention, the stent holder having a stent mounting portion in Configuration J and a support interfacing portion.

FIG. 14 shows a stent (4) mounted on a stent holder (1) having a stent mounting portion (2) in Configuration J, as shown, a support interfacing portion (3), a mask (5) for masking at least part of the stent inner surface, and an electrically chargeable section (8) comprising electrically chargeable threads (11) winding around the stent holder central axis, shown in phantom (43). Examples of suitable materials for the mask (5) include non-conductive materials, polymers, and/or non-stick materials such as polytetrafluoroethylene (e.g., TEFLON).

Figure 15:
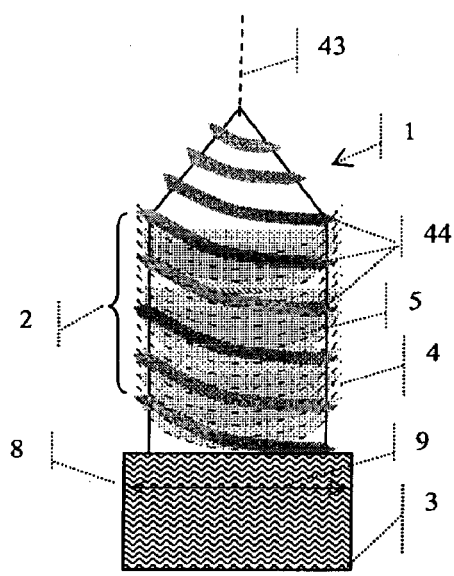
FIG. 15 illustrates a stent holder in accordance with an embodiment of the invention, the stent holder having a stent mounting portion in Configuration K and a support interfacing portion.

FIG. 15 shows a stent (4) mounted on a stent holder (1) having a stent mounting portion (2) in Configuration K, as shown, a support interfacing portion (3), a mask (5) for masking at least part of the stent inner surface, and an electrically chargeable section (8) wherein the stent mounting portion comprises non-conductive threads (44) winding around the stent holder central axis, shown in phantom (43). Examples of suitable materials for the mask (5) and for the non-conductive threads (44) include non-conductive materials, polymers, and/or non-stick materials such as polytetrafluoroethylene (e.g., TEFLON).

In another embodiment, a variation of FIG. 15, the mask (5) is spaced apart from the stent (4) to control the amount and/or the quality of the inner surface coating.

FIGS. 16 to 21 show a stent (4) mounted on a stent holder (1), the stent holder (1) having a stent mounting portion (2) of Configuration A, and having a support interfacing portion (3) of varying configurations. In alternative embodiments, the stent mounting portion (2) is any of Configurations A through K, or other embodiments within the scope of this invention. The support interfacing portion (3) comprises a conductive material and is electrically charged by a support 12. Examples of suitable conductive materials to conduct a charge from the holders to the stent include, but are not limited to, stainless steel and shape memory metal alloys, such as Nitinol (a Ni—Ti alloy).

In FIGS. 16 to 19 the support interfacing portion (3) of these embodiments has an expanded state and comprises at least one arm (30) which supports and electrically couples the stent holder (1) to a support coupling portion (13) of a support (12). In other embodiments, the support interfacing portion (3) also has a collapsed state. In the embodiments of FIGS. 16 to 19, the support interfacing portion (3) in its expanded state exerts force on the inner surface of the support coupling portion (13) of a support (12) in opposing directions, thereby holding the stent holder (1) in place.

Figure 16:
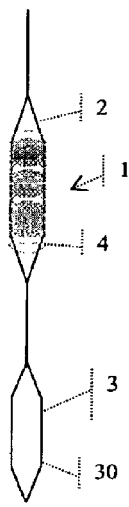
FIG. 16 illustrates a stent holder in accordance with an embodiment of the invention with a mounted stent, the stent holder having a stent mounting portion in Configuration A as shown in FIG. 3A, and having a support interfacing portion in Configuration L.

In the embodiment of FIG. 16, the support interfacing portion Configuration L has an arm (30) that comprises portions approximately parallel to each other.

Figure 17:
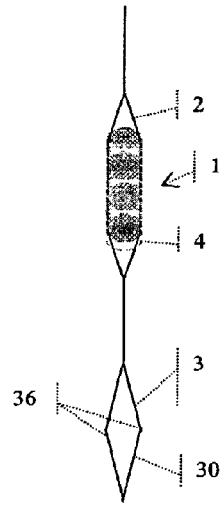
FIG. 17 illustrates a stent holder in accordance with an embodiment of the invention with a mounted stent, the stent holder having a stent mounting portion in Configuration A as shown in FIG. 3A, and having a support interfacing portion in Configuration M.

In the embodiment of FIG. 17, the support interfacing portion Configuration M has an arm (30) extending from a central axis of the stent holder (1), making a plurality of bends, and returning to the central axis of the stent holder. In the embodiment depicted in FIG. 17, the number of contact points (36) between the support interfacing portion (3) and the support coupling portion (13) of the support (12) is two. Alternative embodiments may change the number of contact points by changing the geometry of the support interfacing portion.

Figure 18:
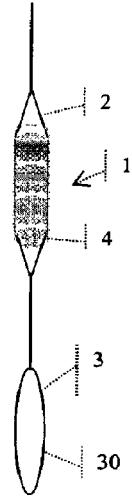
FIG. 18 illustrates a stent holder in accordance with an embodiment of the invention with a mounted stent, the stent holder having a stent mounting portion in Configuration A as shown in FIG. 3A, and having a support interfacing portion in Configuration N.

In the embodiment of FIG. 18, the support interfacing portion is in Configuration N and an arm (30) extending from a central axis of the stent holder and arcing to return to the central axis of the stent holder (1).

Figure 19:
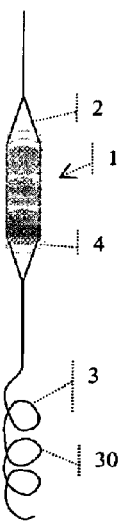
FIG. 19 illustrates a stent holder in accordance with an embodiment of the invention with a mounted stent, the stent holder having a stent mounting portion in Configuration A as shown in FIG. 3A, and having a support interfacing portion in Configuration O.

FIG. 19 illustrates a stent holder (1) having a stent mounting portion (2) in Configuration A as shown in FIG. 3A, and having a support interfacing portion (3) in Configuration O. The support interfacing portion (3) comprises a spring section (6) which electrically couples the stent holder (1) to the support (12) by removably mating with the support coupling portion (13) of the support (12).

Figure 20:
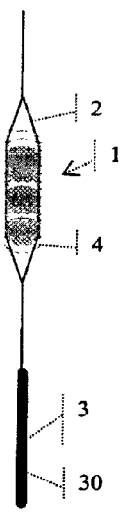
FIG. 20 illustrates a stent holder in accordance with an embodiment of the invention with a mounted stent, the stent holder having a stent mounting portion in Configuration A as shown in FIG. 3A, and having a support interfacing portion in Configuration P.

FIG. 20 illustrates a stent holder (1) having a stent mounting portion (2) in Configuration A as shown in FIG. 3A, and having a support interfacing portion (3) in Configuration P. In alternative embodiments of the invention, the support interfacing portion comprises a pin, rod, mandrel, or wire.

Figure 21:
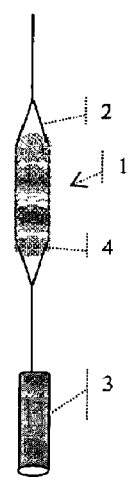
FIG. 21 illustrates a stent holder in accordance with an embodiment of the invention with a mounted stent, the stent holder having a stent mounting portion in Configuration A as shown in FIG. 1A, and having a support interfacing portion in Configuration Q.

In the embodiment of FIG. 21 illustrates a stent holder (1) having a support interfacing portion in Configuration Q, wherein the support interfacing portion (3) is a tube for mating with the support coupling portion (13) of a support (12).

2. The Assembly

FIGS. 22 to 26 illustrate various embodiments of an assembly comprising at least one stent holder for removably holding and electrically charging a stent during a coating process, and a support for supporting the at least one stent holder, wherein the support electrically charges the stent holder. The support is charged by an electrical source. The stent holder is coupled to a support, thereby transferring the electrical charge of the support to the stent holder. The electrical charge of the stent holder is transferred to the mounted stent. The electrically charged holders form electrical fields around the stents which results in attraction of non-charged coating particles to the charged stent during the coating process. The stent holders can be selected from any appropriately mating stent holder support interfacing portion embodiments noted in this specification, and any embodiments that those of skill in the art will be readily able to apply without departing from the scope of the claims hereto attached. Examples of suitable conductive materials for the support in order to conduct a charge from the electrical source to the stent holder include, but are not limited to, stainless steel and shape memory metal alloys, such as Nitinol (a Ni—Ti alloy).

Figure 22:
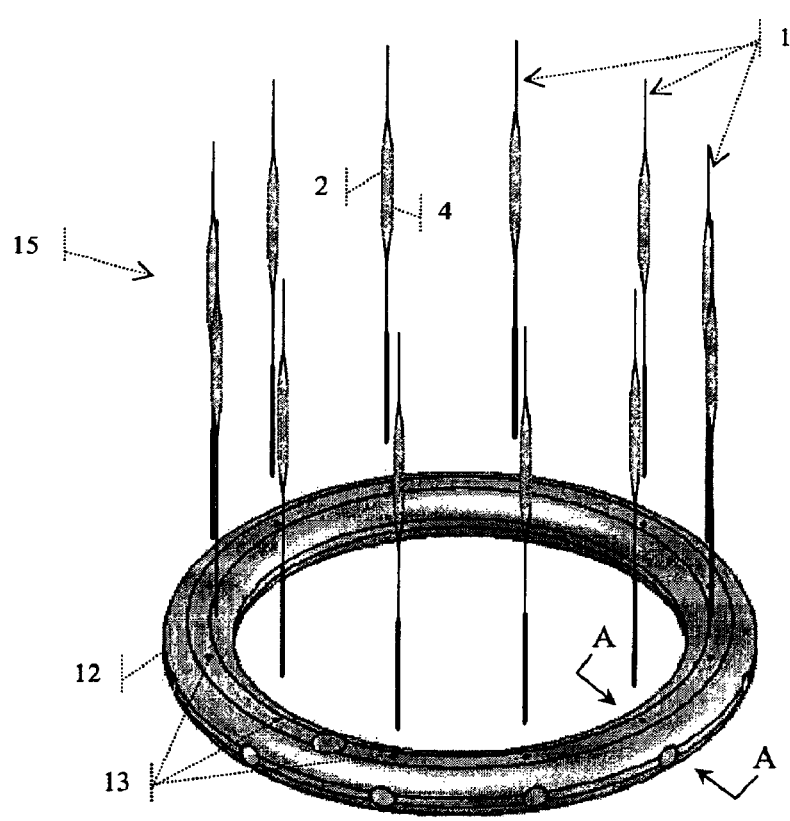
FIG. 22 is an exploded view of an assembly in accordance with an embodiment of the invention, having a stent holder as shown in FIG. 3A, the stent holder having a stent mounting portion in Configuration A as shown in FIG. 3A, and a support interfacing portion in Configuration P as shown in FIG. 20.

FIG. 22 is an exploded view of an assembly (15) in accordance with an embodiment of the invention. In this embodiment, the assembly (15) comprises: at least one stent holder (1) comprising a stent mounting portion (2) in Configuration A as shown in FIG. 3A, and a support having a support interfacing portion in Configuration P as shown in FIG. 20. The support (12) supports the stent holder (1) and electrically charges the stent holder (1). The stent holder (1) removably holds a stent (4) during a coating process and charges the stent (4).

In another embodiment of the assembly (15), a single support (12) comprises a plurality of stent holders (1). In another embodiment, the assembly (15) comprises a support (12) having a plurality of support coupling portions (13) arranged in a circular configuration, and a plurality of stent holders (1) corresponding to the support coupling portion (13) configuration. A central hole of the support (12) provides coating equipment access to the mounted and charged stents (4). Example coating equipment comprises coating nozzles, purging nozzles, electrical field manipulation members, and grounding members.

FIGS. 23 to 26 show embodiments of support coupling portions (13) of a support (12) of an assembly (15), wherein the support coupling portions (13) removably couple and electrically charge a stent holder 1.

Figure 23:
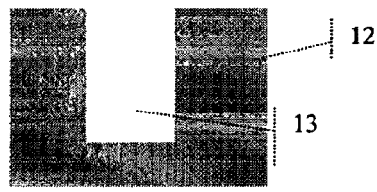
FIG. 23 illustrates a cross sectional view along line A-A of FIG. 22 of the support of an assembly in accordance with an embodiment of the invention, the support having a support coupling portion in Configuration R.

FIG. 23 illustrates a cross sectional view of the support (12) of an assembly (15) along line A-A of FIG. 22 in accordance with an embodiment of the invention, the support (15) comprising a support coupling portion (13) in Configuration R. The support coupling portion (13) of FIG. 23 comprises a hole, a bore or a tube within the support. Non-exhaustive examples of stent holder support interfacing portions which appropriately mate with this embodiment are Configurations L, M, N, 0, and P of FIGS. 16 to 20, respectively.

Figure 24:
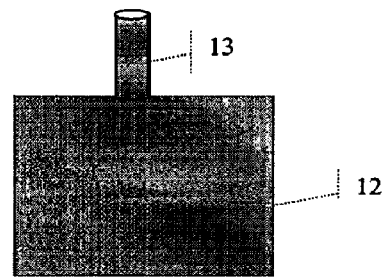
FIG. 24 illustrates a cross sectional view along line A-A of FIG. 22 of the support of an assembly in accordance with an embodiment of the invention, the support having a support coupling portion in Configuration S.

FIG. 24 illustrates a cross sectional view of the support (12) of an assembly (15) along line A-A of FIG. 22 in accordance with an embodiment of the invention, the support (12) comprising a support coupling portion (13) in Configuration S. The support coupling portion (13) of FIG. 24 comprises tube at least a portion of which is outside the support. In this embodiment the support coupling portion (13) is on the top of the support (12). Non-exhaustive examples of stent holder support interfacing portions which appropriately mate with this embodiment are Configurations L, M, N, 0, and P of FIGS. 16 to 20, respectively.

Figure 25:
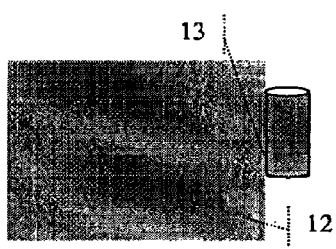
FIG. 25 illustrates a cross sectional view along line A-A of FIG. 22 of the support of an assembly in accordance with an embodiment of the invention, the support having a support coupling portion in Configuration T.

FIG. 25 shows a cross sectional view of the support (12) of an assembly (15) along line A-A of FIG. 22 in accordance with an embodiment of the invention, the support (12) comprising a support coupling portion (13) in Configuration T. In this embodiment, similar to the embodiment of FIG. 24, the support coupling portion (13) of FIG. 25 comprises tube at least a portion of which is outside the support (12). In the embodiment shown in FIG. 25, the support coupling portion (13) is on the side of the support (12). Non-exhaustive examples of stent holder (1) support interfacing portions (3) which appropriately mate with this embodiment are Configurations L, M, N, 0, and P of FIGS. 16 to 20, respectively.

Figure 26:
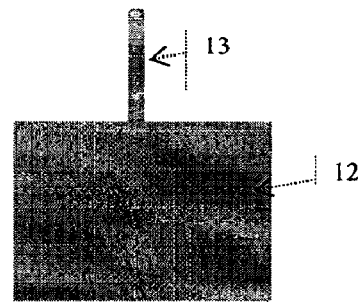
FIG. 26 illustrates a cross sectional view along line A-A of FIG. 22 of the support of an assembly in accordance with an embodiment of the invention, the support having a support coupling portion in Configuration U.

FIG. 26 illustrates a cross sectional view along line A-A of FIG. 22 of the support (12) of an assembly (15) in accordance with an embodiment of the invention, the support (12) having a support coupling portion (13) in Configuration U. In this embodiment, the support coupling portion (13) comprises a conductive wire, rod, mandrel or similar supporting conductive member. A non-exhaustive example of a stent holder (1) support interfacing portion (3) which appropriately mates with this embodiment is Configuration Q of FIG. 21.

While the description is presented in terms of the preferred embodiment, a vascular stent, the invention may be directed to any type of substrate selected from the group consisting of stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic substrates, vertebral disks, bone substitutes, anastomotic substrates, perivascular wraps, colostomy bag attachment substrates, hemostatic barriers, vascular implants, vascular supports, tissue adhesives, tissue sealants, tissue scaffolds and intraluminal substrates. In another embodiment, the assembly comprises the substrate, wherein the substrate is mounted on a substrate holder, wherein the substrate holder electrically charges the substrate, and wherein the substrate holder is supported by a support, wherein the support electrically charges the substrate holder, the support comprising substrate holder coupling portions for electrically charging the substrate holder.

3. The Chamber

Figure 27:
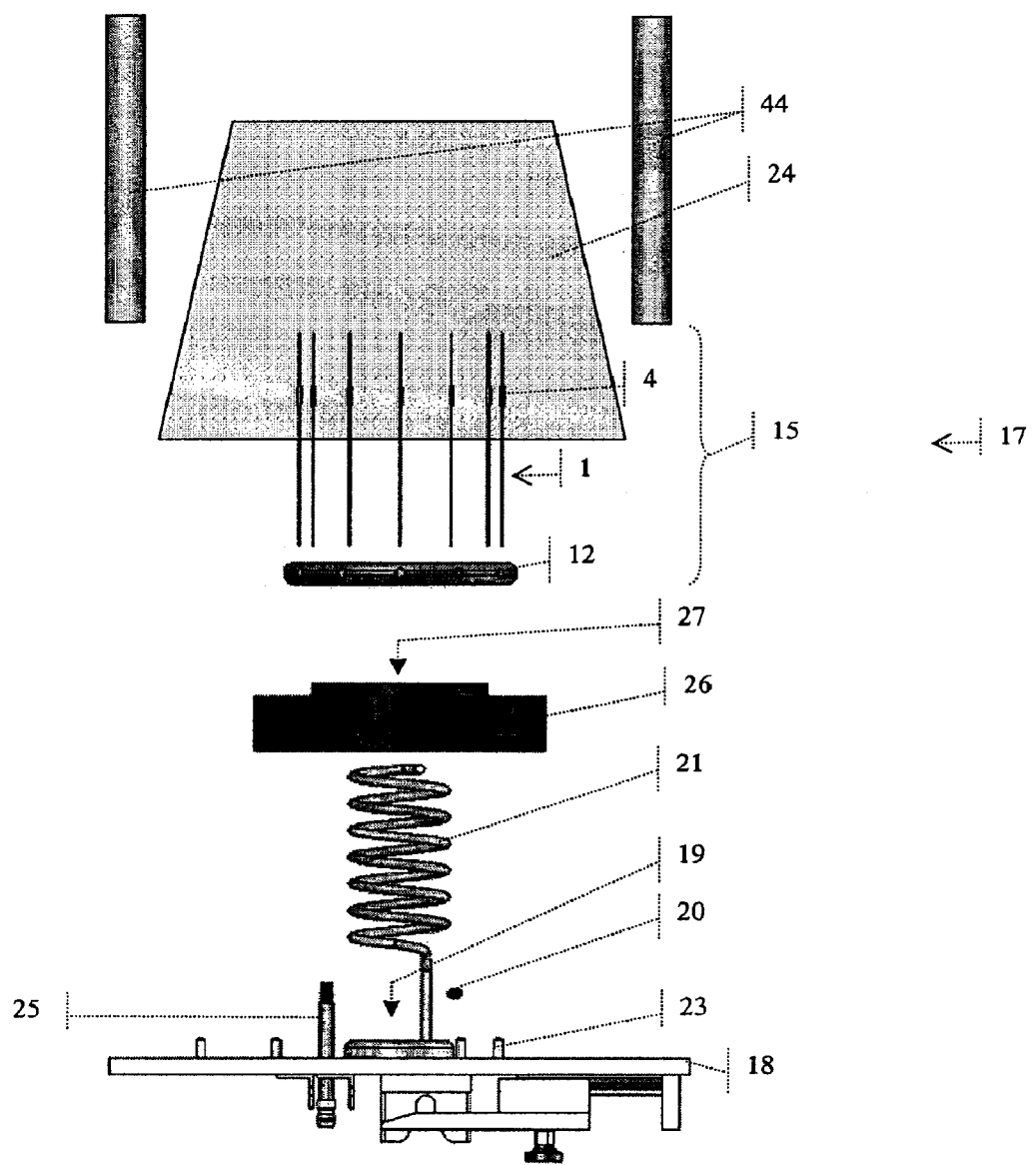
FIG. 27 is an exploded view of a chamber in accordance with an embodiment of the invention.

FIG. 27 is an exploded view of a chamber (17) for a stent coating process in accordance with one embodiment of the invention. This chamber (17) embodiment comprises:
  a base (18) comprising at least one hole (19);
  an assembly (15) comprising: at least one stent holder (1) for removably holding a stent (4) during a coating process wherein the stent holder (1) charges the stent (4) during the coating process, and a support (12) for supporting the at least one stent holder (1), wherein the support (12) electrically charges the stent holder (1);
  and a coating nozzle (20) for coating the stent (4) held by the assembly (15),
wherein the assembly (15) sits on the base (18), wherein the hole (19) in the base (18) provides the coating nozzle (20) access to the chamber (17) for coating the stent (4), and wherein the coating nozzle (20) is removably fitted in the base hole (19).

This embodiment further comprises at least one grounded member (21) connected to a ground source, wherein the at least one grounded member (21) is removably fitted in a base hole (19). The chamber (17) embodiment shown in FIG. 27 further comprises a purge nozzle (23) for purging the chamber (17), wherein the purge nozzle (23) is fitted in a base hole (19). The embodiment further comprises an insulating stand (26) for insulating the base (18) from the electrical charge of the assembly (15), wherein the assembly (15) sits on the insulating stand (26), and the insulating stand (26) sits on the base (18), and wherein the insulating stand (26) has a hole (27) aligning with a base hole (19). The embodiment further comprises a cover (24) that fits over the assembly (15) and sits on the base (18), and comprises an insulating grounded member (44) outside the cover (24), wherein the insulating grounded member (44) is connected to a ground source and removably sits on the base (18). In this embodiment, the cover (24) is transparent, comprises an insulator material, and is disposable. The base (18) has non-conductive properties and is a thermoformed plastic part. The chamber (17) comprises an electrical source (25) connected to the support (12) of the assembly. In another embodiment, the assembly (15) of the chamber (17) comprises a plurality of stent holders (1) arranged in a circular configuration and wherein the coating nozzle (20) is positioned within the circular configuration formed by the holders (1).

While the description is presented in terms of the preferred embodiment, a vascular stent, the invention may be directed to any type of substrate selected from the group consisting of stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic substrates, vertebral disks, bone substitutes, anastomotic substrates, perivascular wraps, colostomy bag attachment substrates, hemostatic barriers, vascular implants, vascular supports, tissue adhesives, tissue sealants, tissue scaffolds and intraluminal substrates. In one embodiment, a chamber comprises:
  an assembly comprising: a substrate holder, wherein a substrate is removably mounted on the substrate holder, wherein the substrate holder electrically charges the substrate; a support, wherein support supports the substrate holder and wherein the support electrically charges the substrate holder, and wherein the support comprises a substrate holder coupling portion for electrically charging the substrate holder;
  a mounted substrate, wherein the substrate is electrically charged;
  a base comprising a first hole;
  and a coating nozzle for coating the substrate held by the assembly,
wherein the assembly sits on the base, wherein the hole in the base provides the coating nozzle access to the chamber for coating the substrate, and wherein the coating nozzle is removably fitted in the first hole.

In another embodiment, the chamber further comprises at least one grounded member connected to a ground source, wherein the at least one grounded member is removably fitted in the first or a second base hole. In another embodiment, the chamber further comprises a purge nozzle for purging the chamber, wherein the purge nozzle is fitted in the first, the second, or a third base hole. In another embodiment, the chamber further comprises an insulating stand for insulating the base from the electrical charge of the assembly, wherein the assembly sits on the insulating stand, and the insulating stand sits on the base, and wherein the insulating stand has a hole aligning with the first, the second, the third, or a fourth base hole. In another embodiment, the chamber further comprises a cover that fits over the assembly and sits on the base, and comprises an insulating grounded member outside the cover, wherein the insulating grounded member is connected to a ground source and removably sits on the base. In another embodiment, the cover is transparent, comprises an insulator material, and is disposable. In another embodiment, the base has non-conductive properties and is a thermoformed plastic part.

In another embodiment, the chamber comprises an electrical source connected to the support of the assembly.

In another embodiment of the chamber, the assembly comprises a plurality of substrate holders arranged in a circular configuration, and wherein the coating nozzle is positioned within the circular configuration formed by the holders.

4. The Method

In one aspect, the invention provides a method of coating a plurality of stents wherein the method comprises:
providing an assembly comprising a support and a plurality of stent holders, wherein the stent holders are arranged in a circular configuration, and wherein a coating nozzle is positioned within the circular configuration formed by the stent holders;
mounting the stents onto the stent holders;
electrically charging the stents by electrically charging the support which electrically charges the stent holder upon which the stents are mounted; and
exposing the electrically charged stents to coating particles from the coating nozzle wherein the electrically charged stents attract the coating particles and wherein the coating particles deposit on the stents while maintaining the stents stationary during coating.

In another embodiment, the coating particles comprise inert polymers, pharmaceutical or biological agents. In another embodiment, the coating particles and exposure of the stent to the coating particles comprise the embodiments as described in PCT/U.S. 06/027,321.

While the description is presented in terms of the preferred embodiment, a vascular stent, the invention may be directed to any type of substrate selected from the group consisting of stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic substrates, vertebral disks, bone substitutes, anastomotic substrates, perivascular wraps, colostomy bag attachment substrates, hemostatic barriers, vascular implants, vascular supports, tissue adhesives, tissue sealants, tissue scaffolds and intraluminal substrates. In one embodiment, the invention provides a method of coating a plurality of substrates wherein the method comprises:
providing an assembly comprising a support and a plurality of substrate holders, wherein the substrate holders are arranged in a circular configuration, and wherein a coating nozzle is positioned within the circular configuration formed by the substrate holders;
mounting the substrates onto the substrate holders;
electrically charging the substrates by electrically charging the support which electrically charges the substrate holder upon which the substrates are mounted; and
exposing the electrically charged substrates to coating particles from the coating nozzle wherein the electrically charged substrates attract the coating particles and wherein the coating particles deposit on the substrates while maintaining the substrates stationary during coating.

5. Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., vascular stents, peripheral stents), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to organic polymers (including stable or inert polymers and biodegradable polymers), metals, inorganic materials such as silicon, and composites thereof, including layered structures with a core of one material and one or more coatings of a different material. Substrates made of a conducting material facilitate electrostatic capture. However, the invention contemplates the use of electrostatic capture in conjunction with substrate having low conductivity or which non-conductive. To enhance electrostatic capture when a non-conductive substrate is employed, the substrate is processed while maintaining a strong electrical field in the vicinity of the substrate.

Subjects into which biomedical implants of the invention may be applied or inserted include both human subjects (including male and female subjects and infant, juvenile, adolescent, adult and geriatric subjects) as well as animal subjects (including but not limited to dog, cat, horse, monkey, etc.) for veterinary purposes.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz Shaz. In another embodiment the biomedical implant is a self-expanding intraluminal vascular stent (e.g., comprising a memory metal such as Ni—Ti, or Nitinol) that can be delivered with a catheter to dilate and expand the lumen of a blood vessel.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds. Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Polyorthoesters, Poly(N-(2-hydroxypropyl)methacrylamide), Poly(1-aspartamide), etc.

Having thus described the preferred embodiments of the present invention, those of skill in the art will be readily able to apply the teachings found herein to yet other embodiments without departing from the scope of the claims hereto attached.

We claim:

1. A stent holder for removeably holding a stent during a coating process wherein the stent holder comprises
    a stent mounting portion comprising at least two arms upon which the stent is mounted, the at least two arms defining a hollow space therebetween, and
    an electrically chargeable section separate from the stent mounting portion,
    wherein the arms form an elliptical portion configured to exert force on an inner surface of the stent,
    wherein the arms are coupled to the electrically chargeable section that electrically charges the stent during the coating process and at least a portion of the electrically chargeable section includes a dimension larger than an inner diameter of the stent so that the stent sits on the electrically chargeable section, and
    wherein when the elliptical portion exerts force on the inner surface of the stent, the arms diverge from a central axis of the stent holder, making at least one bend, and converge at the central axis of the stent holder, or the arms diverge from a central axis of the stent holder and arc to converge at the central axis of the stent holder, the arms touching one another both where the arms diverge and where the arms converge.

2. The stent holder of claim 1, wherein the electrically chargeable section comprises at least one of a memory metal, or stainless steel.

3. The stent holder of claim 1, wherein the holder is disposable.

4. The stent holder of claim 1, wherein the holder comprises a mask for masking at least a part of the stent.

5. The stent holder of claim 4, wherein the mask comprises at least one of a polymer, a non-stick material, or a non-conducting material.

6. The stent holder of claim 1, wherein the holder comprises a support interfacing portion for interfacing with a support, wherein the support supports and electrically charges the support interfacing portion.

7. The stent holder of claim 1, wherein the stent slides over the elliptical portion of the stent holder.

8. The stent holder of claim 1, wherein the stent mounting portion has a collapsed and an expanded state, wherein the collapsed state reduces contact between the stent mounting portion and the stent during stent removal or stent placement on the stent mounting portion.

9. The stent holder of claim 8, wherein the stent mounting portion in the expanded state has an outer diameter approximately equal to the stent inner diameter for securely mounting the stent while minimizing stent deformation.

10. The stent holder of claim 9, wherein the stent mounting portion comprises a mask for masking at least a part of the stent.

11. The stent holder of claim 10, wherein the mask comprises at least one of a polymer, or a non-stick material.

12. The stent holder of claim 9, wherein the stent mounting portion comprises a spring section.

13. The holder of claim 1, wherein the holder further comprises a member for manipulating the electrical field around the stent.

* * * * *